United States Patent
Pule et al.

(10) Patent No.: US 10,730,942 B2
(45) Date of Patent: Aug. 4, 2020

(54) PROTEIN-BASED T-CELL RECEPTOR KNOCKDOWN

(71) Applicant: UCL Business LTD, London (GB)

(72) Inventors: Martin Pule, London (GB); Paul Maciocia, Ricksmanworth (GB); Ben Grimshaw, Cambridge (GB)

(73) Assignee: UCL Business Ltd (GB)

( * ) Notice: Subject to any disclaimer, the term of this patent is extended or adjusted under 35 U.S.C. 154(b) by 0 days.

(21) Appl. No.: 15/657,981

(22) Filed: Jul. 24, 2017

(65) Prior Publication Data

US 2018/0086831 A1    Mar. 29, 2018

(30) Foreign Application Priority Data

Jul. 25, 2016 (CA) ..................................... 2937157

(51) Int. Cl.
| | | |
|---|---|---|
| A61K 35/17 | (2015.01) |
| C07K 16/28 | (2006.01) |
| C12N 15/86 | (2006.01) |
| A61P 35/02 | (2006.01) |
| A61P 35/00 | (2006.01) |
| A61P 37/06 | (2006.01) |
| A61K 39/00 | (2006.01) |
| C12N 5/0783 | (2010.01) |
| A61K 35/00 | (2006.01) |
| A61K 38/00 | (2006.01) |

(52) U.S. Cl.
CPC ........ *C07K 16/2809* (2013.01); *A61K 39/001* (2013.01); *A61K 39/0008* (2013.01); *A61K 39/0011* (2013.01); *A61P 35/00* (2018.01); *A61P 35/02* (2018.01); *A61P 37/06* (2018.01); *C12N 5/0636* (2013.01); *C12N 15/86* (2013.01); *A61K 35/00* (2013.01); *A61K 38/00* (2013.01); *A61K 2039/5156* (2013.01); *A61K 2039/5158* (2013.01); *C07K 2317/56* (2013.01); *C07K 2317/622* (2013.01); *C07K 2317/76* (2013.01); *C07K 2317/80* (2013.01); *C07K 2319/04* (2013.01); *C07K 2319/05* (2013.01); *C07K 2319/74* (2013.01); *C12N 2510/00* (2013.01); *C12N 2740/10043* (2013.01)

(58) Field of Classification Search
None
See application file for complete search history.

(56) References Cited

U.S. PATENT DOCUMENTS

| | | | |
|---|---|---|---|
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,837,028 A | 6/1989 | Allen |
| 4,946,787 A | 8/1990 | Eppstein et al. |
| 4,987,355 A | 1/1991 | Leaper et al. |
| 5,049,386 A | 9/1991 | Eppstein et al. |
| 6,514,752 B1 | 2/2003 | Kucherlapati et al. |
| 2002/0142000 A1* | 10/2002 | Digan .................. A61K 39/395 424/183.1 |
| 2011/0158957 A1* | 6/2011 | Bonini ...................... C12N 9/22 424/93.7 |
| 2016/0022736 A1 | 1/2016 | Feng et al. |
| 2017/0066827 A1* | 3/2017 | Pule ..................... C07K 14/7051 |

FOREIGN PATENT DOCUMENTS

| | | |
|---|---|---|
| WO | 91/16024 A1 | 10/1991 |
| WO | 91/17524 A1 | 11/1991 |
| WO | 2013/074916 A1 | 5/2013 |
| WO | 2013/166051 A1 | 11/2013 |
| WO | 2015/136001 A1 | 9/2015 |
| WO | WO2015132598 | * 11/2015 |

OTHER PUBLICATIONS

Garcia et al., Cell, 2005, 122: 333-336.*
Janeway et al., Immunobiology, 5th Ed., Garland Science, 2001, pp. 106-108.*
Manning et al., Immunity, 1998, 8:413-425.*
Ngo et al., in the Protein Folding Problem and Tertiary Structure Prediction, 1994, Merz, et al., (ed.), Birkhauser, Boston, MA, pp. 433 and 492-495.*
Ahmadi et al., CD3 limits the efficacy of TCR gene therapy in vivo Blood, Sep. 29, 2011 vol. 118, No. 13 pp. 3528-3537.*
Luo et al Stable Enhanced Green Fluorescent Protein Expression After Differentiation and Transplantation of Reporter Human Induced Pluripotent Stem Cells Generated by AAVS1 Transcription Activator-Like Stem Cells Translationalmedicine 2014;3:821-835.*
Ahmad et al., "Antibody-mediated Specific Binding and Cytotoxicity of Liposome-entrapped Doxorubicin to Lung Cancer Cells in Vitro1" (1992) Cancer Res. 52:4817-4820.
Alabi et al., Multiparametric approach for the evaluation of lipid nanoparticles for siRNA delivery (2013) Proc Natl Acad Sci U S A. 110(32):12881-6.
Behr et al., "Gene Transfer with Synthetic Cationic Amphiphiles: Prospects for Gene Therapy" (1994) Bioconjugate Chem. 5:382-389.
Bejarano and Gonzalez, "Motif Trap: a rapid method to clone motifs that can target proteins to defined subcellular localisations" (1999) Journal of Cell Science. 112: 4207-4211.
Beverley and Callard, "Distinctive functional characteristics of human "T" lymphocytes defined by E rosetting or a monoclonal anti-T cell antibody" (1981) Eur. J. Immunol. 11: 329-334.
Blaese et al., "Vectors in cancer therapy: how will they deliver?" (1995) Cancer Gene Ther. 2:291-297.
Bonifant et al., "Toxicity and management in CAR T-cell therapy" (2016) Molecular Therapy—Oncolytics. 3, 16011.

(Continued)

*Primary Examiner* — Maria G Leavitt
(74) *Attorney, Agent, or Firm* — Norton Rose Fulbright US LLP

(57) ABSTRACT

The invention relates to protein-based T-cell receptor knockdown, and its use in T-cell therapies.

4 Claims, 7 Drawing Sheets

Specification includes a Sequence Listing.

(56) References Cited

OTHER PUBLICATIONS

Call et al., "Molecular mechanisms for the assembly of the T cell receptor—CD3 complex" (2004) Mol. Immunol. 40: 1295-1305.
Crystal, "Transfer of Genes to Humans: Early Lessons and Obstacles to Success" (1995) Science. 270:404-410.
Donnelly et al., "The 'cleavage' activities of foot-and-mouth disease virus 2A site-directed mutants and naturally occurring '2A-like' sequences" (2001) J Gen Virol. 82(Pt 5): 1027-1041.
Gao et al., "Cationic liposome-mediated gene transfer" (1995) Gene Therapy 2:710-722.
Jiang et al., "Lipidoid-coated Iron Oxide Nanoparticles for Efficient DNA and siRNA delivery" (2013) Nano Lett. 13 (3):1059-64.
Karagiannis et al., "Rationally Designed Tumor-Penetrating Nanocomplexes" (2012) ACS Nano. 6(10):8484-7.
Kazuki et al., " Human Artificial Chromosomes for Gene Delivery and the Development of Animal Models" (2011) Mol. Ther. 19(9): 1591-1601.
Kouprina et al., "Human artificial chromosomebased gene delivery vectors for biomedicine and biotechnology" (2014) Expert Opinion on Drug Delivery. 11(4): 517-535.
Lee et al., "Molecularly Self-Assembled Nucleic Acid Nanoparticles for Targeted In Vivo siRNA Delivery" (2012) Nat Nanotechnol. 7(6):389-93.
Niegi et al., "LocSigDB: a database of protein localization signals" (2015) LocSigDB: a database of protein localization signals, Database (Oxford) 1-7.
Pule et al., "Artificial T-cell receptors" (2003) Cytotherapy. 5(3): 211-226.
Remy et al., "Gene Transfer with a Series of Lipophilic DNA-Binding Molecules" (1994) Bioconjugate Chem. 5:647-654.
Whitehead et al., "The in Vitro-in Vivo Translation of Lipid Nanoparticles for Hepatocellular siRNA Delivery" (2012) ACS Nano. 6(8):6922-9.
Zhang et al., "Lipid-Modified Aminoglycoside Derivatives for in vivo siRNA Delivery" (2013) Adv Mater. 25(33):4641-5.
Grimshaw, Benjamin David "Developing a universal T cell for use in adoptive immunotherapy" Thesis UCL (2015).
Holler et al., "Expression of a dominant T-cell receptor can reduce toxicity and enhance tumor protection of allogeneic T-cell therapy" (2016) Haematologica. 101:482-490.
Matsunaga et al., "Activation of Antigen-Specific Cytotoxic T Lymphocytes by β2-Microglobulin or TAP1 Gene Disruption and the Introduction of Recipient-Matched MHC Class I Gene in Allogeneic Embryonic Stem Cell-Derived Dendritic Cells" (2008) J Immunol. 181(9):6635-43.
Pelham, Hugh R.B. "Using Sorting Signals to Retain Proteins in Endoplasmic Reticulum" (2000) Methods Enzymol. 327:279-283.
Poirot et al., "Multiplex Genome-Edited T-cell Manufacturing Platform for "Off-the-Shelf" Adoptive T-cell Immunotherapies" (2015) Cancer Res. 75(18):3853-64.
Provasi et al., "Editing T cell specificity towards leukemia by zinc-finger nucleases and lentiviral gene transfer" (2012) Nat. Med. 18:807-815.

* cited by examiner

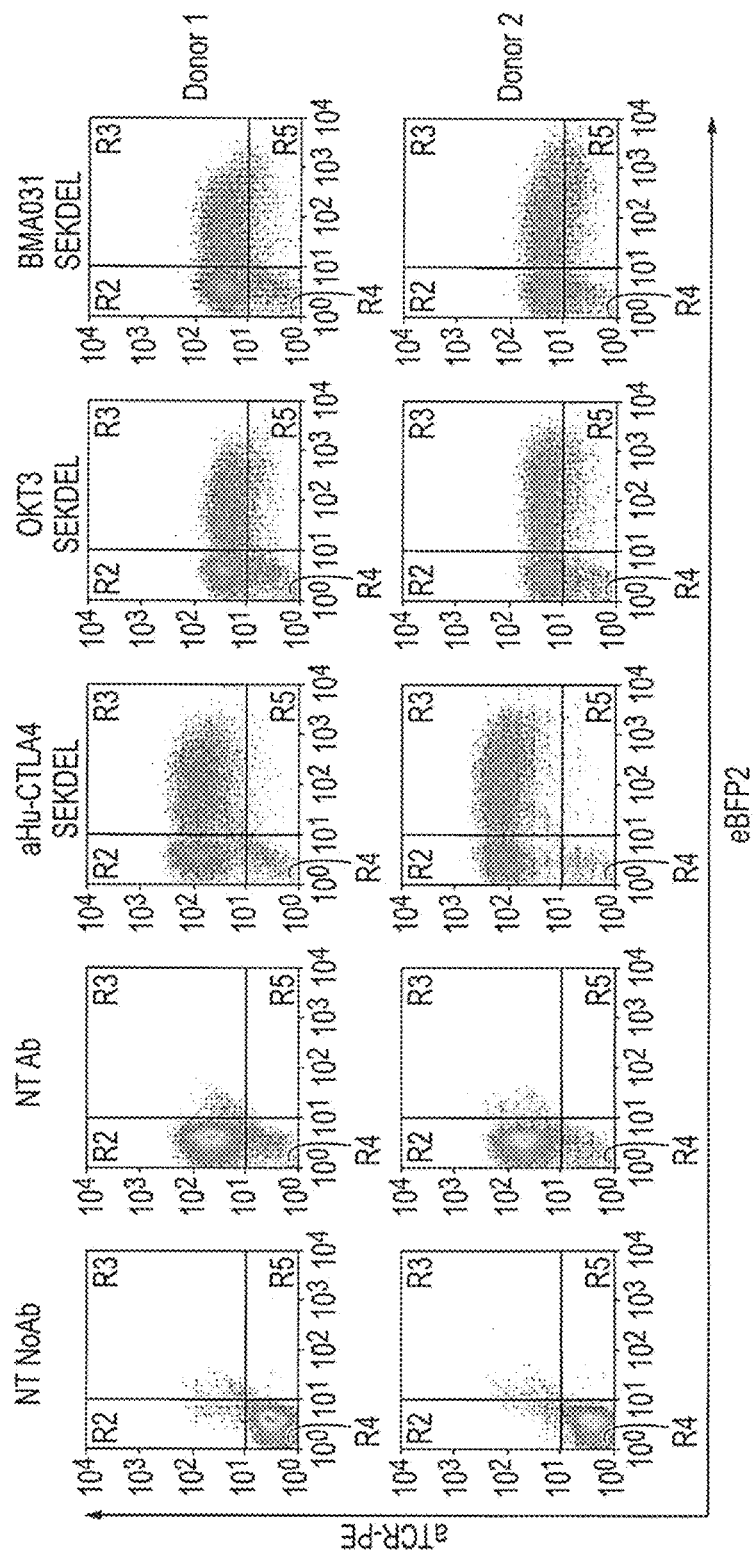

Fig. 2

>S-UCHT1-KDEL

<---signal---><--- VH ---
METDTLLLWVLLLWVPGDIQMTQSPSSLSASVGNRVTITCRASQDIRNYLNWYQQKPGKAPKLLIYYTSR ---><--- linker --->
LESGVPSRFSGSGSGTDYTLTISSLQPEDFATYYCQQGNTLPWTFGQGTKVEIKSGGGGSGGGGSGGGGS ---><--- VL ---
EVQLVESGGGLVQPGGSLRLSCAASGYSFTGYTMNWVRQAPGKGLEWVALINPYKGVSTYNQKFKDRFTI ---><link><kdel>
SVDKSKNTAYLQMNSLRAEDTAVYYCARSGYYGDSDWYFDVWGQGTLVTVSSDPAEPSEKDEL

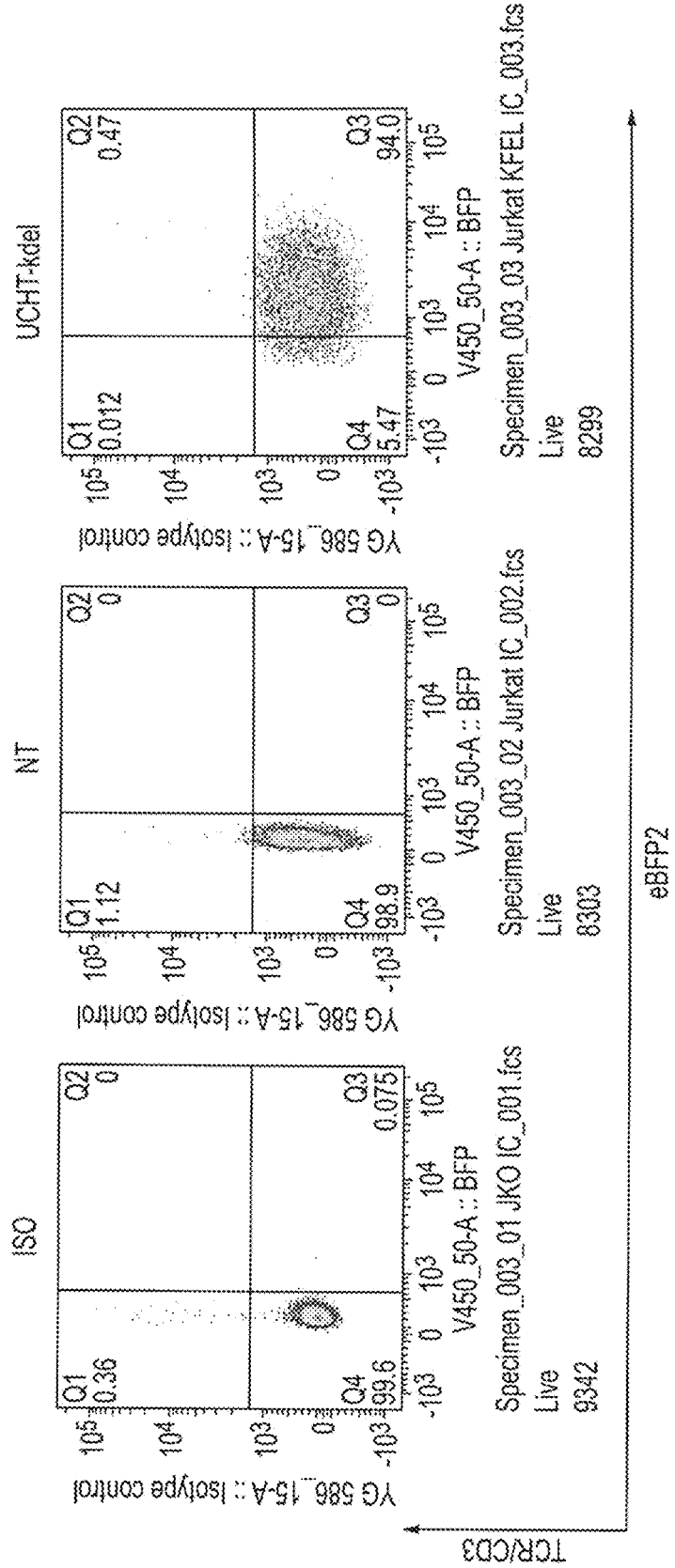

Fig. 6

UCHT1 (Humanised)

VL

DIQMTQSPSSLSASVGNRVTITCRAS QDIRNY LNWYQQKPGKAPKLLIY YTS RLESGVPSRFSGSGSGTD
YTLTISSLQPEDFATYYC QQGNTLPWT FGQGTKVEIK

VH

EVQLVESGGGLVQPGGSLRLSCAAS GYSFTGYT MNWVRQAPGKGLEWVAL INPYKGVS TYNQKFKDR
FTISVDKSKNTAYLQMNSLRAEDTAVYYC ARSGYYGDSDWYFDV WGQGTLVTVS

JOVI-1 (Murine)

VL

DVVMTQSPLSLPVSLGDQASISC RSSQRLVHSNGNTYLH WYLQKPGQSPKLLIY RVSNRFP GVPDRFSG
SGSGTDFTLKISRVEAEDLGIYFC SQSTHVPYT FGGGTKLEIKR

VH

EVRLQQSGPDLIKPGASVKMSCKAS GYTFTGY VMHWVKQRPGQGLEWIGF INPYNDD IQSNERFRGK
ATLTSDKSSTTAYMELSSLTSEDSAVYYCAR GAGYNFDGAYRFFDF WGQGTTLTVS

SEQUENCE LISTING

```
<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: CDR1 of UCHT1 (Humanised) VH

<400> SEQUENCE: 1

Gly Tyr Ser Phe Thr Gly Tyr Thr
1               5

<210> SEQ ID NO 2
<211> LENGTH: 8
<212> TYPE: PRT
<213> ORGANISM: Artificial Sequence
<220> FEATURE:
<223> OTHER INFORMATION: CDR2 of UCHT1 (Humanised) VH

<400> SEQUENCE: 2

Ile Asn Pro Tyr Lys Gly Val Ser
1               5

<210> SEQ ID NO 3
<211> LENGTH: 15
<212> TYPE: PRT
<213> ORGANISM: Artificial Sequence
<220> FEATURE:
<223> OTHER INFORMATION: CDR3 of UCHT1 (Humanised) VH

<400> SEQUENCE: 3

Ala Arg Ser Gly Tyr Tyr Gly Asp Ser Asp Trp Tyr Phe Asp Val
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: CDR1 of UCHT1 (Humanised) VL

<400> SEQUENCE: 4

Gln Asp Ile Arg Asn Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: CDR2 of UCHT1 (Humanised) VL

<400> SEQUENCE: 5

Tyr Thr Ser
1
```

-continued

```
<210> SEQ ID NO 6
<211> LENGTH: 9
<212> TYPE: PRT
<213> ORGANISM: Artificial Sequence
<220> FEATURE:
<223> OTHER INFORMATION: CDR3 of UCHT1 (Humanised) VL

<400> SEQUENCE: 6

Gln Gln Gly Asn Thr Leu Pro Trp Thr
1               5

<210> SEQ ID NO 7
<211> LENGTH: 121
<212> TYPE: PRT
<213> ORGANISM: Artificial Sequence
<220> FEATURE:
<223> OTHER INFORMATION: HCVR of UCHT1 (Humanised)

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: LCVR of UCHT1 (Humanised)

<400> SEQUENCE: 8

Asp Ile Gln Met Thr Gln Ser Pro Ser Ser Leu Ser Ala Ser Val Gly
1               5                   10                  15

Asn Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105
```

<210> SEQ ID NO 9
<211> LENGTH: 7
<212> TYPE: PRT
<213> ORGANISM: Mus musculus

<400> SEQUENCE: 9

Gly Tyr Thr Phe Thr Gly Tyr
1               5

<210> SEQ ID NO 10
<211> LENGTH: 6
<212> TYPE: PRT
<213> ORGANISM: Mus musculus

<400> SEQUENCE: 10

Asn Pro Tyr Asn Asp Asp
1               5

<210> SEQ ID NO 11
<211> LENGTH: 15
<212> TYPE: PRT
<213> ORGANISM: Mus musculus

<400> SEQUENCE: 11

Gly Ala Gly Tyr Asn Phe Asp Gly Ala Tyr Arg Phe Phe Asp Phe
1               5                   10                  15

<210> SEQ ID NO 12
<211> LENGTH: 16
<212> TYPE: PRT
<213> ORGANISM: Mus musculus

<400> SEQUENCE: 12

Arg Ser Ser Gln Arg Leu Val His Ser Asn Gly Asn Thr Tyr Leu His
1               5                   10                  15

<210> SEQ ID NO 13
<211> LENGTH: 7
<212> TYPE: PRT
<213> ORGANISM: Mus musculus

<400> SEQUENCE: 13

Arg Val Ser Asn Arg Phe Pro
1               5

<210> SEQ ID NO 14
<211> LENGTH: 9
<212> TYPE: PRT
<213> ORGANISM: Mus musculus

<400> SEQUENCE: 14

Ser Gln Ser Thr His Val Pro Tyr Thr
1               5

<210> SEQ ID NO 15
<211> LENGTH: 123
<212> TYPE: PRT
<213> ORGANISM: Mus musculus

<400> SEQUENCE: 15

Glu Val Arg Leu Gln Gln Ser Gly Pro Asp Leu Ile Lys Pro Gly Ala
1               5                   10                  15

Ser Val Lys Met Ser Cys Lys Ala Ser Gly Tyr Thr Phe Thr Gly Tyr
            20                  25                  30

-continued

Val Met His Trp Val Lys Gln Arg Pro Gly Gln Gly Leu Glu Trp Ile
            35                  40                  45

Gly Phe Ile Asn Pro Tyr Asn Asp Asp Ile Gln Ser Asn Glu Arg Phe
    50                  55                  60

Arg Gly Lys Ala Thr Leu Thr Ser Asp Lys Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Thr Leu Thr Val Ser
        115                 120

<210> SEQ ID NO 16
<211> LENGTH: 113
<212> TYPE: PRT
<213> ORGANISM: Mus musculus

<400> SEQUENCE: 16

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Val Pro Tyr Thr Phe Gly Gly Gly Thr Lys Leu Glu Ile Lys
            100                 105                 110

Arg

<210> SEQ ID NO 17
<211> LENGTH: 4
<212> TYPE: PRT
<213> ORGANISM: Artificial Sequence
<220> FEATURE:
<223> OTHER INFORMATION: KDEL target peptide sequence

<400> SEQUENCE: 17

Lys Asp Glu Leu
1

<210> SEQ ID NO 18
<211> LENGTH: 15
<212> TYPE: PRT
<213> ORGANISM: Adenovirus

<400> SEQUENCE: 18

Lys Tyr Lys Ser Arg Arg Ser Phe Ile Asp Glu Lys Lys Met Pro
1               5                   10                  15

<210> SEQ ID NO 19
<211> LENGTH: 10
<212> TYPE: PRT
<213> ORGANISM: Homo sapiens

<400> SEQUENCE: 19

```
Met His Arg Arg Arg Ser Arg Ser Cys Arg
1               5                   10
```

<210> SEQ ID NO 20
<211> LENGTH: 6
<212> TYPE: PRT
<213> ORGANISM: Artificial Sequence
<220> FEATURE:
<223> OTHER INFORMATION: SEKDEL retention sequence

<400> SEQUENCE: 20

```
Ser Glu Lys Asp Glu Leu
1               5
```

<210> SEQ ID NO 21
<211> LENGTH: 273
<212> TYPE: PRT
<213> ORGANISM: Artificial Sequence
<220> FEATURE:
<223> OTHER INFORMATION: S-UCHT1-KDEL

<400> SEQUENCE: 21

```
Met Glu Thr Asp Thr Leu Leu Leu Trp Val Leu Leu Leu Trp Val Pro
1               5                   10                  15

Gly Asp Ile Gln Met Thr Gln Ser Pro Ser Ser Leu Ser Ala Ser Val
            20                  25                  30

Gly Asn Arg Val Thr Ile Thr Cys Arg Ala Ser Gln Asp Ile Arg Asn
        35                  40                  45

Tyr Leu Asn Trp Tyr Gln Gln Lys Pro Gly Lys Ala Pro Lys Leu Leu
    50                  55                  60

Ile Tyr Tyr Thr Ser Arg Leu Glu Ser Gly Val Pro Ser Arg Phe Ser
65                  70                  75                  80

Gly Ser Gly Ser Gly Thr Asp Tyr Thr Leu Thr Ile Ser Ser Leu Gln
                85                  90                  95

Pro Glu Asp Phe Ala Thr Tyr Tyr Cys Gln Gln Gly Asn Thr Leu Pro
            100                 105                 110

Trp Thr Phe Gly Gln Gly Thr Lys Val Glu Ile Lys Ser Gly Gly Gly
        115                 120                 125

Gly Ser Gly Gly Gly Gly Ser Gly Gly Gly Gly Ser Glu Val Gln Leu
    130                 135                 140

Val Glu Ser Gly Gly Gly Leu Val Gln Pro Gly Gly Ser Leu Arg Leu
145                 150                 155                 160

Ser Cys Ala Ala Ser Gly Tyr Ser Phe Thr Gly Tyr Thr Met Asn Trp
                165                 170                 175

Val Arg Gln Ala Pro Gly Lys Gly Leu Glu Trp Val Ala Leu Ile Asn
            180                 185                 190

Pro Tyr Lys Gly Val Ser Thr Tyr Asn Gln Lys Phe Lys Arg Asp Phe
        195                 200                 205

Thr Ile Ser Val Asp Lys Ser Lys Asn Thr Ala Tyr Leu Gln Met Asn
    210                 215                 220

Ser Leu Arg Ala Glu Asp Thr Ala Val Tyr Tyr Cys Ala Arg Ser Gly
225                 230                 235                 240

Tyr Tyr Gly Asp Ser Asp Trp Tyr Phe Asp Val Trp Gly Gln Gly Thr
                245                 250                 255

Leu Val Thr Val Ser Ser Asp Pro Ala Glu Pro Ser Glu Lys Asp Glu
            260                 265                 270
```

Leu

```
<210> SEQ ID NO 22
<211> LENGTH: 107
<212> TYPE: PRT
<213> ORGANISM: Artificial Sequence
<220> FEATURE:
<223> OTHER INFORMATION: UCHT1(Humanised) VL

<400> SEQUENCE: 22

Asp Ile Gln Met Thr Gln Ser Pro Ser Ser Leu Ser Ala Ser Val Gly
1               5                   10                  15

Asn Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 23
<211> LENGTH: 121
<212> TYPE: PRT
<213> ORGANISM: Artificial Sequence
<220> FEATURE:
<223> OTHER INFORMATION: UCHT1 (Humanised) VH

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser
        115                 120

<210> SEQ ID NO 24
<211> LENGTH: 113
<212> TYPE: PRT
<213> ORGANISM: Mus musculus

<400> SEQUENCE: 24

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Arg Leu Val His Ser
```

```
                    20                  25                  30

Asn Gly Asn Thr Tyr Leu His Trp Tyr Leu Gln Lys Pro Gly Gln Ser
            35                  40                  45

Pro Lys Leu Leu Ile Tyr Arg Val Ser Asn Arg Phe Pro Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Ile Tyr Phe Cys Ser Gln Ser
                85                  90                  95

Thr His Val Pro Tyr Thr Phe Gly Gly Gly Thr Lys Leu Glu Ile Lys
            100                 105                 110

Arg

<210> SEQ ID NO 25
<211> LENGTH: 123
<212> TYPE: PRT
<213> ORGANISM: Mus musculus

<400> SEQUENCE: 25

Glu Val Arg Leu Gln Gln Ser Gly Pro Asp Leu Ile Lys Pro Gly Ala
 1               5                  10                  15

Ser Val Lys Met Ser Cys Lys Ala Ser Gly Tyr Thr Phe Thr Gly Tyr
            20                  25                  30

Val Met His Trp Val Lys Gln Arg Pro Gly Gln Gly Leu Glu Trp Ile
        35                  40                  45

Gly Phe Ile Asn Pro Tyr Asn Asp Asp Ile Gln Ser Asn Glu Arg Phe
     50                  55                  60

Arg Gly Lys Ala Thr Leu Thr Ser Asp Lys Ser Ser Thr Thr Ala Tyr
 65                  70                  75                  80

Met Glu Leu Ser Ser Leu Thr Ser Glu Asp Ser Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Thr Leu Thr Val Ser
        115                 120

<210> SEQ ID NO 26
<211> LENGTH: 4
<212> TYPE: PRT
<213> ORGANISM: Artificial Sequence
<220> FEATURE:
<223> OTHER INFORMATION: KKXX target peptide motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 26

Lys Lys Xaa Xaa
 1

<210> SEQ ID NO 27
<211> LENGTH: 5
<212> TYPE: PRT
<213> ORGANISM: Artificial Sequence
<220> FEATURE:
<223> OTHER INFORMATION: KXKXX target peptide motif
<220> FEATURE:
<221> NAME/KEY: misc_feature
<222> LOCATION: (2)..(2)
<223> OTHER INFORMATION: Xaa can be any naturally occurring amino acid
```

-continued

```
<220> FEATURE:
<221> NAME/KEY: misc_feature
<222> LOCATION: (4)..(5)
<223> OTHER INFORMATION: Xaa can be any naturally occurring amino acid

<400> SEQUENCE: 27

Lys Xaa Lys Xaa Xaa
1               5
```

PROTEIN-BASED T-CELL RECEPTOR KNOCKDOWN

CROSS-REFERENCE TO RELATED APPLICATIONS

This application claims the benefit of priority to Canadian Patent Application No. 2,937,157 filed Jul. 25, 2016, which is hereby incorporated by reference in its entirety.

FIELD OF THE INVENTION

The invention relates to protein-based T-cell receptor knockdown, and its use in T-cell therapies.

BACKGROUND TO THE INVENTION

Chimeric antigen receptor (CAR) T-cells graft the specificity of a monoclonal antibody (mAb) to a T-cell (Pule, M., Finney, H. & Lawson, A. Artificial T-cell receptors. Cytotherapy 5, 211-226 (2003)). CAR T-cells are usually autologous—i.e. they are generated from the patient's own lymphocytes. This is effective and simple but has a number of limitations: (1) it may be difficult or impossible to generate a product from patient's own lymphocytes due to insufficient quantity or quality of lymphocytes consequent to disease or chemotherapy; (2) there may be insufficient time to generate an autologous CAR T-cell product due to the tempo of the patient's illness; and (3) autologous production requires a bespoke product to be manufactured for each patient which makes manufacture costly.

An alternative approach is to generate "off-the-shelf" CAR T-cells from healthy donor lymphocytes. Cord blood lymphocytes are a particularly convenient source of donor lymphocytes for off-the-shelf CAR T-cell production. Using the off-the-shelf approach, production of the CAR T-cell product is independent of the patient. Furthermore, if the manufacturing process lends itself to economies of scale, the off-the-shelf approach may advantageously reduce the cost of production of the CAR T-cell product.

Given the wide variability of human leukocyte antigen (HLA) types, it is very likely that any off-the-shelf CAR T-cell product will be completely HLA-mismatched from the recipient. It is simply not feasible to have a HLA-matched, off-the-shelf CAR T-cell product ready for every recipient in need thereof. This HLA mismatch is associated with its own technical challenges, in particular graft versus-host disease (GVHD). In GVHD, that native T-cell receptor (TCR) of T-cells in donated tissue (the "graft") recognise antigens in the recipient (the "host") as foreign. Thus, transplanted T-cells attack host cells and tissues, causing damage to the host organs. Acute or fulminant GVHD, which normally occurs within the first 100 days following transplant, is associated with significant morbidity and mortality. Chronic GVHD, which normally occurs after 100 days following transplant, adversely influences long-term survival.

GVHD typically occurs in the setting of allogeneic haematopoietic stem cell transplantation (HSCT), in which the donor and recipient are fully or partially HLA-matched. In the off-the-shelf CAR T-cell approach, the CAR T-cell product and the recipient are completely HLA-mismatched. When the donor and recipient are not matched, more severe type of GVHD known as "transfusion-associated GVHD" (TA-GVHD) occurs.

In order to be of widespread utility, an off-the-shelf CAR T-cell product must cause, at most, a minimal amount of GVHD when administered to a HLA-mismatched recipient. Current approaches to attenuating the ability of HLA-mismatched CAR T-cells to cause GVHD involve editing the genome of the CAR T-cells to disrupt native TCR expression, using zinc finger nucleases (ZFNs), transcription activator-like effector nucleases (TALENs), or the clustered regularly interspaced short palindromic repeats (CRISPR)/Cas system. These genome editing methods can disrupt a gene, entirely knocking out all of its output. However, several problems are associated with these genome editing approaches. Firstly, the genes required for these approaches typically have to be delivered separately to CAR T-cells during their production, for instance by electroporation with synthetic mRNA. Consequently, the resultant disruption or knockdown of the native TCR in the T-cell is not linked to CAR expression. This means that sorting for CAR-expressing T-cells does not necessarily also sort for T-cells expressing the genome editing genes required to disrupt native TCR expression. Likewise, sorting for expression of genome editing genes does not necessarily sort for CAR-expression. Therefore, to obtain CAR T-cells suitable for use in an off-the-shelf product, it is necessary to perform two different sorting steps, one to select for CAR-expressing T-cells and one to select for T-cells expressing the genome editing genes. Secondly, ZFNs, TALENS and CRISPR/Cas can all introduce off-target gene disruptions and cause unwanted translocations.

An improved method of disrupting the expression of the native TCR in CAR T-cells is therefore required.

SUMMARY OF THE INVENTION

This invention relates to a novel mechanism by which to disrupt surface expression of the native TCR in T-cells, such as CAR T-cells. The mechanism employed in the invention is not associated with the disadvantages currently experienced with the existing, genome editing approaches to disruption of the native T-cell receptor.

The inventors have surprising found that a molecule comprising a binding portion comprising a binding domain which binds to one or more components of TCR/CD3 complex, and a retention portion comprising a retention domain that retains the one or more components within the endoplasmic reticulum (ER) or Golgi apparatus may be used to disrupt the expression of native TCR on the surface of a T-cell. By disrupting the surface expression of native TCR, the capacity of the T-cell to cause GVHD following transfer to a HLA-mismatched patient is reduced or completely eliminated. Thus, the present invention relates the provision of "universal" therapeutic T-cell, such as a CAR T-cell, for inclusion in an off-the-shelf immunotherapy product.

In the following description, references to expression of native TCR refer to surface expression of functional TCR/CD3 complex.

When the T-cell is a CAR T-cell, the CAR and the molecule which disrupts expression of the native TCR may be introduced to the T-cell together, using a nucleic acid construct that comprises a first nucleic acid sequence encoding the molecule and a second nucleic acid sequence encoding the CAR. As set out in detail below, the first and second nucleic acid sequences may be linked by a nucleic acid sequence that allows the molecule and the CAR to be processed as separate, unfused protein products. In this way, expression of the molecule may be linked to expression of the CAR. Thus, sorting for CAR-expressing T-cells also sorts for T-cells expressing the molecule that disrupts native TCR expression. Likewise, sorting for expression of the molecule that disrupts native TCR expression also sorts for CAR-expression. Therefore, only one sorting step is required to obtain CAR T-cells suitable for use in an off-the-shelf product.

Accordingly, the invention provides a molecule which disrupts the expression of native TCR in a T-cell, which molecule comprises a binding domain which binds to one or more components of TCR/CD3 complex, and a retention portion comprising a retention domain that retains the one or more components within the ER or Golgi apparatus.

The invention also provides:

a nucleic acid sequence encoding a molecule of the invention, comprising a nucleic acid sequence encoding a binding portion comprising a binding domain which binds to one or more components of the TCR/CD3 complex, and a retention portion comprising a retention domain that retains the one or more components within the ER or Golgi apparatus;

a nucleic acid construct comprising a first nucleic acid sequence of the invention, and a second nucleic acid sequence which encodes a chimeric antigen receptor (CAR);

a nucleic acid construct comprising a first nucleic acid sequence of the invention, and a second nucleic acid sequence which encodes a suicide gene;

a vector comprising the nucleic acid sequence of the invention or a nucleic acid construct of the invention;

a method for producing a T-cell expressing a molecule of the invention, comprising: transfecting or transducing a T-cell with a nucleic acid sequence of the invention or a nucleic acid construct of the invention; and expressing the molecule in the T-cell;

a T-cell comprising (a) a nucleic acid sequence of the invention or a nucleic acid construct of the invention, or (b) a vector of the invention;

a method for reducing or completely eliminating expression of native TCR in a T-cell, comprising (a) providing a nucleic acid sequence of the invention or a nucleic acid construct of the invention, or a vector encoding the nucleic acid sequence or nucleic acid construct; (b) transfecting or transducing the T-cell with the nucleic acid sequence, nucleic acid construct or vector; and (c) expressing the molecule in the T-cell;

a method for producing a T-cell having reduced or completely eliminated expression of native TCR, comprising (a) providing a T-cell; (b) transfecting or transducing the T-cell with a nucleic acid sequence of the invention or a nucleic acid construct of the invention, or a vector encoding the nucleic acid sequence or nucleic acid construct; and (c) expressing the molecule in the T-cell;

a method of reducing or preventing graft versus host disease (GVHD) in a patient associated with the administration of one or more CAR T-cells to the patient, comprising (a) transfecting or transducing the one or more CAR T-cells with a nucleic acid sequence of the invention or a nucleic acid construct of the invention, or a vector encoding the nucleic acid sequence or nucleic acid construct; and (b) administering the CAR T-cells to the patient;

a method of reducing or preventing GVHD in a patient associated with the transfusion of one or more CAR T-cells to the patient, comprising (a) generating the one or more CAR T-cells by transfecting or transducing one or more T-cells with a nucleic acid construct comprising a first nucleic acid sequence of the invention and a second nucleic acid sequence which encodes a chimeric antigen receptor, or a vector encoding the nucleic acid construct; and (b) administering the CAR T-cells to the patient;

a method of reducing or preventing GVHD in a patient associated with the transfusion of one or more CAR T-cells to the patient, comprising (a) producing one or more T-cells expressing a molecule of the invention by (i) providing one or more T-cells; (ii) transfecting or transducing the one or more T-cells with a nucleic acid sequence of the invention or a nucleic acid construct comprising a first nucleic acid sequence of the invention and a second nucleic acid sequence which encodes a suicide gene, or a vector encoding the nucleic acid sequence or nucleic acid construct; and (iii) expressing the molecule in the one or more T-cells; (b) converting the one or more T-cells into one or more CAR T-cells by transfecting or transducing the one or more T-cells with a construct encoding a CAR and expressing the CAR; and (c) administering the CAR T-cells to the patient;

a nucleic acid sequence of the invention or a nucleic acid construct comprising a first nucleic acid sequence of the invention and a second nucleic acid sequence which encodes a suicide gene for use in a method of reducing or preventing GVHD in a patient associated with the administration of one or more CAR T-cells to the patient, the method comprising (a) transfecting or transducing the one or more CAR T-cells with the nucleic acid sequence or nucleic acid construct and (b) administering the CAR T-cells to the patient;

a nucleic acid construct comprising a first nucleic acid sequence of the invention and a second nucleic acid sequence which encodes a chimeric antigen receptor for use in a method of reducing or preventing GVHD in a patient associated with the administration of one or more CAR T-cells to the patient, the method comprising (a) generating the one or more CAR T-cells by transfecting or transducing one or more T-cells with the nucleic acid construct and (b) administering the CAR T-cells to the patient;

use of a nucleic acid sequence of the invention or a nucleic acid construct comprising a first nucleic acid sequence of the invention and a second nucleic acid sequence which encodes a suicide gene in the manufacture of a medicament for the treatment of cancer or an autoimmune condition, wherein the medicament comprises one or more CAR T cells transfected or transduced with the nucleic acid sequence or nucleic acid construct.

use of a nucleic acid construct comprising a first nucleic acid sequence of the invention and a second nucleic acid sequence which encodes a chimeric antigen receptor in the manufacture of a medicament for the treatment of cancer or an autoimmune condition, wherein the medicament comprises one or more CAR T cells transfected or transduced with the nucleic acid construct;

a method of treating a disease in a patient in need thereof, comprising administering to the patient a therapeutically effective number of CAR T-cells expressing a molecule of the invention; and CAR T-cells expressing a molecule of the invention, for use in a method of treating a disease in a patient in need thereof, the method comprising administering to the patient a therapeutically effective number of cells.

DESCRIPTION OF THE FIGURES

FIG. 1. Peripheral blood T-cells transduced with OKT3 and BMA031 based sekdel constructs. Some knock-down of both transduced and non-transduced populations are seen. Anti-CTLA4 sekdel is used as a control.

FIG. 2. Annotated sequence for S-UCHT1-KDEL (SEQ ID NO:21).

(FIG. 3a) structure of S-UCHT1-sekdel; (FIG. 3b) Mechanism of activity FIGS. 4a and 4b.

FIG. 6. VH and VL sequences for UCHT1 and Jovi. 1. CDRs are shown in bold and highlighted. Shown are SEQ ID NO:22, SEQ ID NO:23, SEQ ID NO:24 and SEQ ID NO:25.

DETAILED DESCRIPTION OF THE INVENTION

Figure 3A:
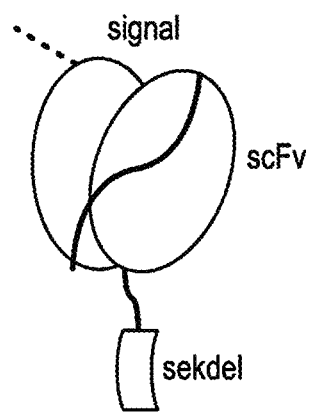
FIGS. 3a and 3b.

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a molecule" includes "molecules", reference to "a T-cell" includes two or more such T-cells, reference to "a component" includes two or more such components, and the like.

All publications, patents and patent applications cited herein, whether supra or infra, are hereby incorporated by reference in their entirety.

Molecule of the Invention

The present invention provides a molecule which disrupts the expression of native TCR in a T-cell, which molecule comprises a binding domain which binds to one or more components of the TCR/CD3 complex, and a retention portion comprising a retention domain that retains the one or more components within the ER or Golgi apparatus.

Disruption of the expression of the native TCR refers to changing the amount of expression of native TCR on the surface of the T-cell. Preferably, the expression of native TCR is reduced or completely eliminated. A T-cell having reduced expression of native TCR has a reduced amount of native TCR on its surface. A T-cell with completely eliminated expression of native TCR has no native TCR on its surface.

Methods for determining surface expression of native TCR are known in the art. For instance, T-cells surface-stained (i.e. stained without a permeablisation step) with an antibody or other molecule that binds to the TCR may be analysed by flow cytometry or fluorescence microscopy. Using flow cytometry, reduction in the mean fluorescence intensity (MFI) of TCR surface-staining in study T-cells compared to control T-cells indicates a reduction in surface expression of native TCR. For instance, the MFI (and thus surface expression) may be reduced by up to 100%, such as up to 99%, up to 98%, up to 95%, up to 90%, up to 85%, up to 80%, up to 75%, up to 70%, up to 60%, up to 50%, up to 40%, or up to 25%, in study T-cells compared to control T-cells. The absence of native TCR expression is indicated by the absence of surface-staining for the native TCR (i.e. by an MFI equivalent or similar to that of a negative control sample).

The TCR/CD3 complex, otherwise known as the T-cell receptor complex, is a multimeric complex on the T-cell surface whose activation leads to the activation of the T-cell. The complex comprises (i) TCR, (ii) CD3 T-cell co-receptor. As set out below, the TCR comprises alpha ($\alpha$) and beta ($\beta$) chains. The CD3 T-cell co-receptor comprises a CD3-gamma (CD3$\gamma$) chain, a CD3-delta (CD3$\delta$) chain, two CD3-epsilon (CD3$\epsilon$) chains and two zeta-chain ($\zeta$-chain) accessory molecules.

TCRs allow for the antigen-specific activation of T-cells. Every T-cell expresses clonal TCRs which recognize specific peptide/MHC complex during physical contact between T-cell and antigen-presenting cell-APC (via MHC class II) or any other cell type (via MHC class I). The TCR is a disulfide-linked membrane-anchored heterodimeric protein normally consisting of the highly variable alpha ($\alpha$) and beta ($\beta$) chains. Each chain of the TCR comprises two extracellular domains: a variable (V) region and a constant (C) region, both of immunoglobulin superfamily (IgSF) domain forming antiparallel $\beta$-sheets. The constant region is proximal to the cell membrane, followed by a transmembrane region and a short cytoplasmic tail, while the variable region binds to the peptide/MHC complex. The variable domain of the TCR $\alpha$-chain and the TCR $\beta$-chain each have three hypervariable or complementarity determining regions (CDRs), that contribute to the TCR's specificity for a particular peptide/MHC complex. The variable region of the $\beta$-chain also has an additional area of hypervariability (HV4) that does not normally contact antigen.

CD3 is required for the antigen-specific activation of T-cells. In particular, CD3 links antigen recognition by the TCR with intracellular signalling events downstream of the TCR T3 zeta-chain. CD3 is a protein complex comprising six distinct chains. In mammals, CD3 comprises a CD3-gamma (CD3$\gamma$) chain, a CD3-delta (CD3$\delta$) chain, two CD3-epsilon (CD3$\epsilon$) chains and two zeta-chain ($\zeta$-chain) accessory molecules. The CD3-gamma, CD3-delta and CD3-epsilon chains are highly related cell-surface proteins of the immunoglobulin superfamily comprising a single extracellular immunoglobulin domain. The transmembrane region of the CD3 chains is negatively charge, allowing the chains to associated with TCR chains, which are positively charged. The zeta-chain (also known as T-cell surface glycoprotein CD3 zeta-chain or CD247) plays an important role in coupling antigen recognition to several intracellular signal-transduction pathways. Low expression of the zeta-chain results in an impaired immune response.

Accordingly, TCR/CD3 normally comprises several components: TCR $\alpha$-chain, TCR $\beta$-chain, CD3-gamma chain, CD3-delta chain, two CD3-epsilon chains, and two CD3-zeta-chains. The molecule of the invention binds to one or more of these components. For example, the molecule of the invention may bind to two or more, three or more, four or more, five or more, or six or more of these components. When the molecule binds to two or more of (i) TCR $\alpha$-chain, (ii) TCR $\beta$-chain, (iii) CD3-gamma chain, (iv) CD3-delta chain, (v) CD3-epsilon chain, and (v) zeta-chain, it may bind these components in any combination, i.e. (i,ii); (i,iii); (i,iv); (i,v); (i,vi); (ii,iii); (ii,iv); (ii,v); (ii,vi); (iii,iv); (iii,v); (iii,vi); (iv,v); (iv,vi); (v,vi); (i,ii,iii); (i,ii,iv); (i,ii,v); (i,ii,vi); (i,iii,iv); (i,iii,v); (i,iii,vi); (i,iv,v); (i,iv,vi); (i,v,vi); (ii,iii,iv); (ii,iii,v); (ii,iii,vi); (ii,iv,v); (ii,iv,vi); (ii,v,vi); (iii,iv,v); (iii,iv,vi); (iii,v,vi); (iv,v,vi); (i,ii,iii,iv); (i,ii,iii,v); (i,ii,iii,vi); (i,ii,iv,v); (i,ii,iv,vi); (i,ii,v,vi); (i,iii,iv,v); (i,iii,iv,vi); (i,iii,v, vi); (i,iv,v,vi); (ii,iii,iv,v); (ii,iii,iv,vi); (ii,iii,v,vi); (ii,iv,v,vi); (iii,iv,v,vi); (i,ii,iii,iv,v); (i,ii,iii,iv,vi); (i,ii,iii,v,vi); (i,ii,iv,v,vi); (i,iii,iv,v,vi); (ii,iii,iv,v,vi); or (i,ii,iii,iv,v,vi). The molecule may also bind to two or more (such as three or more, four or more or five or more) of the same component, such as two or more TCR α-chains, two or more TCR β-chains, two or more CD3-gamma chains, two or more CD3-delta chains, two or more CD3-epsilon chains, or two or more zeta-chains.

The one or more components to which binding occurs may be assembled to form the TCR/CD3 complex. That is, the one or more components may be part of a complex comprising TCR α-chain, TCR β-chain, CD3-gamma chain, CD3-delta chain, two CD3-epsilon chains, and two zeta-chains.

Preferably, the one or more components to which bind occurs are not assembled to form the TCR/CD3 complex. That is, the one or more components are preferably not part of a complex comprising TCR α-chain, TCR β-chain, CD3-gamma chain, CD3-delta chain, two CD3-epsilon chains, and two zeta-chains. In other words, binding may occur to a single component that is not associated with any of the other components. Binding may occur to one or more components that are associated with each other but which do not from the full TCR/CD3 complex. Thus, binding may occur to a nascent, incomplete form of the TCR/CD3 complex. In this case, the one or more components may not form any complex. The one or more components may form a complex other than the TCR/CD3 complex. The one or more components may form a complex that comprises some but not all of the other components of the TCR/CD3 complex, such as a complex comprising (i,ii); (i,iii); (i,iv); (i,v); (i,vi); (ii,iii); (ii,iv); (ii,v); (ii,vi); (iii,iv); (iii,v); (iii,vi); (iv,v); (iv,vi); (v,vi); (i,ii,iii); (i,ii,iv); (i,ii,v); (i,ii,vi); (i,iii, iv); (i,iii,v); (i,iii,vi); (i,iv,v); (i,iv,vi); (i,v,vi); (ii,iii,iv); (ii,iii,v); (ii,iii,vi); (ii,iv,v); (ii,iv,vi); (ii,v,vi); (iii,iv,v); (iii, iv,vi); (iii,v,vi); (iv,v,vi); (i,ii,iii,iv); (i,ii,iii,v); (i,ii,iii,vi); (i,ii,iv,v); (i,ii,iv,vi); (i,ii,v,vi); (i,iii,iv,v); (i,iii,iv,vi); (i,iii,v, vi); (i,iv,v,vi); (ii,iii,iv,v); (ii,iii,iv,vi); (ii,iii,v,vi); (ii,iv,v,vi); (iii,iv,v,vi); (i,ii,iii,iv,v); (i,ii,iii,iv,vi); (i,ii,iii,v,vi); (i,ii,iv,v, vi); (i,iii,iv,v,vi); or (ii,iii,iv,v,vi).

T-cell receptor assembly is reviewed by Call et al., (Molecular mechanisms for the assembly of the T-cell receptor-CD3 complex. Mol. Immunol. 40, 1295-1305 (2004)). Assembly results in alignment of polar residues in the transmembrane domain. Each assembly step thus results in the formation of a three-helix interface in the membrane that involves one basic and two acidic transmembrane residues, and this arrangement effectively shields these ionizable residues at protein-protein interfaces from the lipid. Since proteins whose transmembrane domains have exposed ionizable residues are not stably integrated into the lipid bilayer, assembly based on shielding of ionizable residues permits full equilibration of the receptor into the lipid bilayer and prevents degradation. Assembly, export of intact receptor complexes is precisely regulated with degradation of unassembled components. The CD3/TCR complex hence is quite vulnerable to strategies which perturb its assembly, such as binding by the binding portion of the molecule and retention in the ER or Golgi apparatus by the retention portion of the molecule.

The binding domain may be any domain that is capable of binding to one or more of the components of TCR/CD3 complex. Thus, the binding domain may be any domain that is capable of binding to one or more of (i) TCR α-chain, (ii) TCR β-chain, (iii) CD3-gamma chain, (iv) CD3-delta chain, (v) CD3-epsilon chain, and (v) zeta-chain. For instance, the binding domain may bind to (i); (ii); (iii); (iv); (v); (vi); (i,ii); (i,iii); (i,iv); (i,v); (i,vi); (ii,iii); (ii,iv); (ii,v); (ii,vi); (iii,iv); (iii,v); (iii,vi); (iv,v); (iv,vi); (v,vi); (i,ii,iii); (i,ii,iv); (i,ii,v); (i,ii,vi); (i,iii,iv); (i,iii,v); (i,iii,vi); (i,iv,v); (i,iv,vi); (i,v,vi); (ii,iii,iv); (ii,iii,v); (ii,iii,vi); (ii,iv,v); (ii,iv,vi); (ii,v,vi); (iii, iv,v); (iii,iv,vi); (iii,v,vi); (iv,v,vi); (i,ii,iii,iv); (i,ii,iii,v); (i,ii, iii,vi); (i,ii,iv,v); (i,ii,iv,vi); (i,ii,v,vi); (i,iii,iv,v); (i,iii,iv,vi); (i,iii,v,vi); (i,iv,v,vi); (ii,iii,iv,v); (ii,iii,iv,vi); (ii,iii,v,vi); (ii, iv,v,vi); (iii,iv,v,vi); (i,ii,iii,iv,v); (i,ii,iii,iv,vi); (i,ii,iii,v,vi); (i,ii,iv,v,vi); (i,iii,iv,v,vi); (ii,iii,iv,v,vi); or (i,ii,iii,iv,v,vi). Assays suitable for determining the ability of a binding domain to bind to one or more of the components of TCR/CD3 complex are well known in the art, such as Western blotting or enzyme-linked immunosorbent assay (ELISA).

The binding domain preferably binds to one or more of the components of the TCR/CD3 complex, wherein the one or more components are not assembled to form the TCR/CD3 complex. That is, the binding domain preferably binds to the one or more components when they are not part of a complex comprising TCR α-chain, TCR β-chain, CD3-gamma chain, CD3-delta chain, two CD3-epsilon chains, and two zeta-chains.

Preferably, the binding domain may be used to stain intracellularly for one or more of the components of the TCR/CD3 complex. In other words, the binding domain is preferably a molecule that can be used to determine the intracellular presence of one or more components of the TCR/CD3 complex by, for instance, immunofluorescent methods (such as flow cytometry or fluorescence microscopy) or immunohistochemistry. The ability of the binding domain to stain intracellularly for one or more of the components of the TCR/CD3 complex may correlate with the ability of the binding domain to recognise assembling TCR/CD3 complex in a nascent stage before access to the ER or Golgi apparatus has passed.

The binding domain may be a superantigen (SAg), a TCR agonist, an antibody, a monoclonal antibody, a fragment antigen-binding (Fab) fragment, a F(ab')$_2$ fragment, a single chain variable fragment (scFv), a scFv-Fc, or a single domain antibody. The binding domain is a preferably a scFv, a scFv-Fc, a single domain antibody or a monoclonal antibody. The single domain antibody is preferably a camelid antibody, an artificial $V_H$H fragment or an IgNAR. The binding domain is most preferably a scFv.

The binding domain preferably binds to CD3-epsilon. More preferably, the binding domain is a UCHT1 antibody, or is derived from a UCHT1 antibody. Thus, the binding domain may be produced by or derived from a product of a UCHT1 hybridoma.

The binding domain may be a UCHT1-derived scFv, scFv-Fc, single domain antibody or monoclonal antibody. For instance, the binding domain may comprise the heavy chain complementarity determining region (CDR)1, CDR2 and CDR3 sequences of SEQ ID NOs: 1, 2 and 3 respectively. The binding domain may comprise the light chain CDR1, CDR2 and CDR3 sequences of SEQ ID NOs: 4, 5 and 6 respectively. The binding domain may comprise the heavy chain CDR1, CDR2 and CDR3 sequences of SEQ ID NOs: 1, 2 and 3 respectively and the light chain CDR1, CDR2 and CDR3 sequences of SEQ ID NOs: 4, 5 and 6 respectively. The binding domain may comprise a heavy chain variable region (HCVR) comprising the heavy chain CDR1, CDR2 and CDR3 sequences of SEQ ID NOs: 1, 2 and 3 respectively. The binding domain may comprise a light chain variable region (LCVR) comprising the light chain CDR1, CDR2 and CDR3 sequences of SEQ ID NOs:

4, 5 and 6 respectively. The binding domain may comprise a HCVR comprising the heavy chain CDR1, CDR2 and CDR3 sequences of SEQ ID NOs: 1, 2 and 3 respectively and a LCVR comprising the light chain CDR1, CDR2 and CDR3 sequences of SEQ ID NOs: 4, 5 and 6 respectively. The binding domain may comprise the HCVR sequence of SEQ ID NO:7. The binding domain may comprise the LCVR sequence of SEQ ID NO:8. The binding domain may comprise the HCVR sequence of SEQ ID NO:7 and the LCVR sequence of SEQ ID NO:8. The binding domain may comprise three heavy chain CDRs (HCDR1, HCDR2 and HCDR3) contained within the HCVR sequence of SEQ ID NO: 7. The binding domain may comprise three light chain CDRs (LCDR1, LCDR2 and LCDR3) contained within the LCVR sequence of SEQ ID NO: 8. The binding domain may comprise three heavy chain CDRs (HCDR1, HCDR2 and HCDR3) contained within the HCVR sequence of SEQ ID NO: 7 and three light chain CDRs (LCDR1, LCDR2 and LCDR3) contained within the LCVR sequence of SEQ ID NO: 8. The binding domain may comprise a heavy chain comprising the HCVR sequence of SEQ ID NO: 7. The binding domain may comprise a light chain comprising the LCVR sequence of SEQ ID NO: 8. The binding domain may comprise a heavy chain comprising the HCVR sequence of SEQ ID NO: 7 and a light chain comprising the LCVR sequence of SEQ ID NO: 8.

The binding domain may further comprise one or more of the constant domains that are normally included in an UCHT1 antibody (i.e. an antibody produced by an UCHT1 hybridoma). The binding domain may comprise one or more constant domains other than those that are included in an UCHT1 antibody. The binding domain may comprise a combination of one or more of the constant domains that are normally included in an UCHT1 antibody, and one or more constant domains other than those that are included in an UCHT1 antibody.

The binding domain preferably binds to TCR beta chain. More preferably, the binding domain is a Jovi.1 antibody, or is derived from a Jovi.1 antibody. Thus, the binding domain may be produced by or derived from a product of a Jovi.1 hybridoma.

The binding domain may be a Jovi.1-derived derived scFv, scFv-Fc, single domain antibody or monoclonal antibody. For instance, the binding domain may comprise the heavy chain CDR1, CDR2 and CDR3 sequences of SEQ ID NOs: 9, 10 and 11 respectively. The binding domain may comprise the light chain CDR1, CDR2 and CDR3 sequences of SEQ ID NOs: 12, 13 and 14 respectively. The binding domain may comprise the heavy chain CDR1, CDR2 and CDR3 sequences of SEQ ID NOs: 9, 10 and 11 respectively and the light chain CDR1, CDR2 and CDR3 sequences of SEQ ID NOs: 12, 13 and 14 respectively. The binding domain may comprise a HCVR comprising the heavy chain CDR1, CDR2 and CDR3 sequences of SEQ ID NOs: 9, 10 and 11 respectively. The binding domain may comprise a LCVR comprising the light chain CDR1, CDR2 and CDR3 sequences of SEQ ID NOs: 12, 13 and 14 respectively. The binding domain may comprise a HCVR comprising the heavy chain CDR1, CDR2 and CDR3 sequences of SEQ ID NOs: 9, 10 and 11 respectively and a LCVR comprising the light chain CDR1, CDR2 and CDR3 sequences of SEQ ID NOs: 12, 13 and 14 respectively. The binding domain may comprise the HCVR sequence of SEQ ID NO: 15. The binding domain may comprise the LCVR sequence of SEQ ID NO: 16. The binding domain may comprise the HCVR sequence of SEQ ID NO: 15 and the LCVR sequence of SEQ ID NO: 16. The binding domain may comprise three heavy chain CDRs (HCDR1, HCDR2 and HCDR3) contained within the HCVR sequence of SEQ ID NO: 15. The binding domain may comprise three light chain CDRs (LCDR1, LCDR2 and LCDR3) contained within the LCVR sequence of SEQ ID NO: 16. The binding domain may comprise three heavy chain CDRs (HCDR1, HCDR2 and HCDR3) contained within the HCVR sequence of SEQ ID NO: 15 and three light chain CDRs (LCDR1, LCDR2 and LCDR3) contained within the LCVR sequence of SEQ ID NO: 16. The binding domain may comprise a heavy chain comprising the HCVR sequence of SEQ ID NO: 15. The binding domain may comprise a light chain comprising the LCVR sequence of SEQ ID NO: 16. The binding domain may comprise a heavy chain comprising the HCVR sequence of SEQ ID NO: 15 and a light chain comprising the LCVR sequence of SEQ ID NO: 16.

The binding domain may further comprise one or more of the constant domains that are normally included in an Jovi.1 antibody (i.e. an antibody produced by a Jovi.1 hybridoma). The binding domain may comprise one or more constant domains other than those that are included in a Jovi.1 antibody. The binding domain may comprise a combination of one or more of the constant domains that are normally included in an Jovi.1 antibody, and one or more constant domains other than those that are included in an Jovi.1 antibody.

The molecule may comprise two or more, such as three or more, four or more, five or more binding domains. In this case, two or more of the binding domains may be the same. Two or more of the binding domains may be different.

The retention domain may be any domain that retains the one or more components of the TCR/CD3 complex within the ER or Golgi apparatus. The retention domain may be a target peptide. A target peptide is a short peptide chain of 3 to 70 amino acids that directs the transport of a protein to a specific region of the cell, such as the ER or the Golgi apparatus, and/or retains the protein in the specific region. A variety of target peptides are known in the art.

The retention domain is preferably a KDEL sequence (SEQ ID NO:17), a KKXX motif (SEQ ID NO:26), a KXKXX motif (SEQ ID NO:27), a tail of adenoviral E19 protein having sequence KYKSRRSFIDEKKMP (SEQ ID NO:18), or a fragment of HLA invariant chain having sequence MHRRRSRSCR (SEQ ID NO:19). The retention domain is preferably C-terminal to the binding domain. The retention domain may be N-terminal to the binding domain.

The retention domain is preferably a KDEL (Lys-Asp-Glu-Leu)(SEQ ID NO: 17) sequence. KDEL is a target peptide sequence in the amino acid structure of a protein which prevents the protein from being secreted from the ER. A protein having a KDEL sequence will be retrieved from the Golgi apparatus by retrograde transport to the ER lumen. The KDEL sequence may also target proteins from other locations (such as the cytoplasm) to the ER. Proteins can only leave the ER after the KDEL sequence has been cleaved off. Thus, the protein resident in the ER will remain in the ER as long as it contains a KDEL sequence.

The retention domain may be a KKXX (Lys-Lys-xxx-xxx) motif. KKXX is a target peptide motif that is generally located in the C terminus of the amino acid structure of a protein. KKXX is responsible for retrieval of ER membrane proteins from the cis end of the Golgi apparatus by retrograde transport, via interaction with the coat protein (COPI) complex.

The retention domain may be a C-terminal cytoplasmic tail of a known ER protein, such as adenoviral E19 protein. For instance, the binding domain may be a tail of adenoviral E19 protein having sequence KYKSRRSFIDEKKMP (SEQ ID NO: 18). Alternatively, the binding domain may be an N-terminal fragment of the invariant chain of HLA, such as a fragment having sequence MHRRRSRSCR (SEQ ID NO: 19).

Other suitable binding domains are known in the art. For instance, LocSigDB (http://genome.unmc.edu/LocSigDB/) is a database of experimental protein localization signals for eight distinct subcellular locations (Negi et al., LocSigDB: a database of protein localization signals, Database (Oxford), 2015, 1-7). Furthermore, known methods may be used to identify further binding domains that retains the one or more components of the TCR/CD3 complex within the ER or Golgi apparatus (see, for example, Bejarano and Gonzalez, Motif Trap: a rapid method to clone motifs that can target proteins to defined subcellular localisations, Journal of Cell Science, 112, 4207-4211 (1999)).

The molecule may comprise two or more, such as three or more, four or more, five or more retention domains. In this case, two or more of the retention domains may be the same. Two or more of the retention domains may be different.

Nucleic Acid Sequence of the Invention

The invention also provides a nucleic acid sequence encoding a molecule of the invention, comprising a nucleic acid sequence encoding a binding portion comprising a binding domain which binds to one or more components of TCR/CD3 complex, and a retention portion comprising a retention domain that retains the one or more components within the ER or Golgi apparatus.

The nucleic acid sequence may comprise DNA and/or RNA. The nucleic acid sequence may be double stranded or single stranded. For instance, the nucleic acid sequence may comprise dsDNA and/or ssDNA. The nucleic acid sequence may comprise dsRNA and/or ssRNA.

Any of the one or more components, the binding domain or the retention domain may be as discussed above with reference to the molecule of the invention.

Nucleic Acid Constructs of the Invention

The invention further provides a nucleic acid construct comprising a first nucleic acid sequence of the invention, and a second nucleic acid sequence which encodes a CAR.

The nucleic acid construct may comprise DNA and/or RNA. The nucleic acid construct may be double stranded or single stranded. For instance, the nucleic acid construct may comprise dsDNA or ssDNA. The nucleic acid construct may comprise dsRNA and/or ssRNA. Similarly, the first and/or second nucleic acid sequence may comprise DNA and/or RNA. The first and/or second nucleic acid sequence may be double stranded or single stranded. The first and/or second nucleic acid sequence may comprise dsDNA and/or ssDNA. The first and/or second nucleic acid may comprise dsRNA and/or ssRNA.

The construct may comprise two or more, such as three or more, four or more, five or more, six or more, seven or more, eight or more, nine or more, ten or more or twenty or more of each type of nucleic acid sequence.

CARs may be used to re-direct the antigen specificity of a T-cell. CARs typically comprise the heavy ($V_H$) and light ($V_L$) variable fragments from an antibody joined by a short linker to form a scFv. The scFv is attached to a spacer region that allows it to protrude from the cell surface. The spacer region may be the CD8 stalk. A transmembrane domain then links the extracellular domain (ectodomain) to one or more intracellular activation domains. These may be immunoreceptor tyrosine-based inhibition motifs (ITIMs) or immunoreceptor tyrosine-based activation motif (ITAMs) depending on the intracellular signaling pathway to be activated or inhibited. Commonly used intracellular activation domains include the CD3-zeta, CD28, OX40 and 41BB intracellular signaling domains. Thus, ligand binding to the CAR may lead to activation of the intracellular signaling cascade and T-cell activation by initiating phosphorylation of ITAMs. Conversely, ligand binding to the CAR may initiate phosphorylation of ITIMs, giving inhibition of the intracellular signaling cascade and T-cell inhibition.

In this way, CARs are able to activate T-cells in response to target cell surface antigens without the need for major histocompatibility complex (MHC) recognition. Therefore, CARs can easily modify most subsets of T-cells to have increased persistence and improved development of memory. Furthermore, CARs are not restricted to recognition of protein-derived peptides. CARs may recognise other types of cell surface molecule on a target cell, including non-protein structures such as gangliosides and carbohydrate antigens.

Accordingly, the CAR encoded by the second nucleic acid sequence may be specific for an extracellular antigen or a cell surface antigen. The antigen may be a peptide antigen or a non-peptide antigen. The non-peptide antigen may be a carbohydrate antigen, a ganglioside, or a glycolipid. The CAR may be specific for a tumour antigen, a viral antigen, a bacterial antigen, a fungal antigen, a protozoal antigen, a host antigen or a cytokine. The CAR may be specific for one or more antigens associated with acute myeloid leukemia (AML), such as one or more of CD33, CD123 and CLL1.

The provision of a single nucleic acid construct comprising a first nucleic acid sequence of the invention, and a second nucleic acid sequence which encodes a CAR may be advantageous over the provision of two separate amino acid sequences each encoding one of these components. The inclusion of the sequence encoding the molecule of the invention and the sequence encoding a CAR in the same construct allows reduction or abrogation of native TCR expression by the molecule of the invention to be linked with CAR receptor. T-cells transfected or transformed with the construct will express both the molecule of the invention, and a CAR. Therefore, T-cells transfected or transformed with the construct will express the encoded CAR, but will not express (or will express a reduced amount) of native TCR. Therefore, sorting (by e.g. magnetic-activated cell sorting (MACS)) for T-cells that do not express native TCR will also sort for CAR T-cells. Conversely, sorting for CAR T-cells will also sort for cells that do not express native TCR, or express a reduced amount of native TCR.

The nucleic acid construct of the invention may further comprise a third nucleic acid sequence which encodes a suicide gene. The construct may comprise two or more, such as three or more, four or more, or five or more sequences encoding a suicide gene. Suicide genes are discussed in detail below.

The invention also provides a nucleic acid construct comprising a first nucleic acid sequence of the invention, and a second nucleic acid sequence which encodes a suicide gene.

The nucleic acid construct may comprise DNA and/or RNA. The nucleic acid construct may be double stranded or single stranded. For instance, the nucleic acid construct may comprise dsDNA or ssDNA. The nucleic acid construct may comprise dsRNA and/or ssRNA. Similarly, the first and/or second nucleic acid sequence may comprise DNA and/or RNA. The first and/or second nucleic acid sequence may be double stranded or single stranded. The first and/or second nucleic acid sequence may comprise dsDNA and/or ssDNA. The first and/or second nucleic acid may comprise dsRNA and/or ssRNA.

The construct may comprise two or more, such as three or more, four or more, five or more, six or more, seven or more, eight or more, nine or more, ten or more or twenty or more of each type of nucleic acid sequence.

A suicide gene is a gene that causes a cell to kill itself through apoptosis. Activation of these genes can be due to many processes, but the main cellular "switch" to induce apoptosis is the p53 protein. As discussed above, CAR expression can be used to redirect a T-cell's response towards an antigen of interest, for example a tumour antigen or viral antigen. Therefore, CAR T-cells can be used therapeutically to enhance T-cell responses against e.g. tumour cells or virus-infected cells. However, CAR T-cells are also capable of eliciting damaging side-effects in the host. For instance, administration of CAR T-cells may lead to cytokine release syndrome, neurologic toxicity, "on target/off tumour" recognition, anaphylaxis, clonal expansion secondary to insertional oncogenesis, off-target antigen recognition, and, as discussed above, GVHD (Bonifant et al.3 Toxicity and management in CAR T-cell therapy, Molecular Therapy—Oncolytics, 3, Article number: 16011 (2016)). The incorporation of a suicide gene to a CAR T-cell provides a mechanism by which such CAR T-cell induced toxicities may be reduced or eliminated.

The suicide gene encoded by the construct of the invention may therefor act as a safety switch to limit toxicities induced by CAR T-cell administration. Any suitable suicide gene may be used. Suicide genes are well-know in the art. The suicide gene is preferably RQR8, iCasp9 or thymidine kinase. The suicide gene preferably allows cells expressing the suicide gene to be selectively deleted in response to administration of the substance. For example, RQR8 facilitates selective deletion of cells expressing this gene upon exposure to rituximab. Similarly, iCasp9 facilitates selective deletion of cells expressing this gene upon exposure to AP1903. Thymidine kinase allows cells expressing this gene to be killed using ganciclovir.

As the sequence encoding the suicide gene is comprised in the same nucleic acid construct as the sequence encoding the molecule of the invention, the reduction or abrogation of native TCR expression by the molecule of the invention will be linked in cells transformed or transfected with the construct with expression of the suicide gene. T-cells transfected or transformed with the construct will express both the molecule of the invention, and the suicide gene. Therefore, T-cells transfected or transformed with the construct will possess the encoded suicide gene, but will not express (or will express a reduced amount) of native TCR. Therefore, sorting (by e.g. FACS) for T-cells that do not express native TCR will also sort for T-cells possessing the suicide gene. Conversely, sorting for T-cells possessing the suicide gene will also sort for cells that do not express native TCR, or express a reduced amount of native TCR.

In some situations, the construct comprises (a) a nucleic acid sequence encoding the molecule of the invention, (b) a nucleic acid sequence encoding a CAR, and (c) a nucleic acid sequence encoding a suicide gene. In T-cells transfected or transformed with such a construct, expression of the molecule, the CAR and the suicide gene will be coupled. Therefore, T-cells transfected or transformed with the construct will possess the encoded CAR and suicide gene, but will not express (or will express a reduced amount) of native TCR. Therefore, sorting (by e.g. FACS) for T-cells that do not express native TCR will also sort for T-cells possessing the CAR and the suicide gene. Sorting for T-cells possessing the CAR will also sort for cells that possess the suicide gene but do not express (or express a reduced amount of) native TCR. Likewise, sorting for T-cells possessing the suicide gene will also sort for cells that express the CAR but do not express (or express a reduced amount of) native TCR.

As set out above, the construct of the invention comprises two or more nucleic acid sequences, each encoding a different protein. Thus, the construct of the invention encodes multiple different proteins. To allow the multiple proteins to be encoded as polyproteins that dissociate into separate protein products following translation, one or more of the nucleic acid sequences comprised in the construct may be linked by a nucleic acid sequence encoding a self-processing peptide, such as a foot-and-mouth disease 2A-like peptide (2A peptide for short). Foot-and-mouth disease 2A-like peptide is described in detail in Donnelly et al., J Gen Virol. 2001 May; 82 (Pt 5): 1027-1041. Peptide bond formation between glycine and proline residues within the 2A peptide is highly inefficient and, as a result, the proteins encoded by two or more nucleic acid sequences linked by a sequence encoding a 2A peptide will be stoichiometrically processed as multiple unfused protein products.

Vector of the Invention

The invention also provides a vector comprising the nucleic acid sequence of the invention or a nucleic acid construct of the invention.

The vector may be a viral vector. Preferably, the viral vector is a lentivirus, a retrovirus, an adenovirus, an adeno-associated virus (AAV), a vaccinia virus or a herpes simplex virus. Methods for producing and purifying such vectors are know in the art. Preferably, the viral vector is a gamma-retrovirus or a lentivirus. The lentivirus may be a modified HIV virus suitable for use in delivering genes. The lentivirus may be a SIV, FIV, or equine infectious anemia virus (EQIA) based vector. The viral vector may comprise a targeting molecule to ensure efficient transduction with the nucleic acid sequence or nucleic acid construct. The targeting molecule will typically be provided wholly or partly on the surface of the viral vector in order for the molecule to be able to target the virus to T-cells. The viral vector is preferably replication deficient.

The vector may be a non-viral vector. Preferably, the non-viral vector is a DNA plasmid, a naked nucleic acid, a nucleic acid complexed with a delivery vehicle, or an artificial virion. The non-viral vector may be a human artificial chromosome, as described in e.g. Kazuki et al., Mol. Ther. 19 (9): 1591-1601 (2011), and Kouprina et al., Expert Opinion on Drug Delivery 11 (4): 517-535 (2014). When the non-viral vector is a nucleic acid complexed with a delivery vehicle, the delivery vehicle may be a liposome, virosome, or immunoliposome. Integration of a plasmid vector may be facilitated by a transposase such as sleeping beauty or PiggyBAC.

T-Cells of the Invention

The invention provides a T-cell comprising (a) a nucleic acid sequence of the invention or a nucleic acid construct of the invention, or (b) a vector of the invention. Nucleic acid sequences, nucleic acid constructs and vectors are described in detail above.

The T-cell may be any type of T-cell. The T-cell may be a CD4+ T-cell, or helper T-cell ($T_H$ cell), such as a $T_H1$, $T_H2$, $T_H3$, $T_H17$, $T_H9$, or $T_{FH}$ cell. The T-cell may be a CD8+ T-cell, or cytotoxic T-cell. The T-cell may be a CD4+ or CD8+ memory T-cell, such as a central memory T-cell or an effector memory T-cell. The T-cell may be a regulatory T-cell (Treg).

The T-cell may comprise one or more, such as two or more, three or more, four or more, five or more or ten or more, nucleic acid sequences encoding a CAR, independent of any CAR-encoding nucleic acid sequence comprised in the construct or vector of the invention. When the T-cell comprises two or more sequences encoding a CAR, the sequences may encode the same CAR or different CARs. T-cell may therefore express one or more CARs, independent of any CAR expressed from the construct or vector of the invention. Thus, the T-cell may be a CAR.

The T-cell may comprise one or more, such as two or more, three or more, four or more, five or more or ten or more nucleic acid sequences of the invention. Similarly, the T-cell may comprise one or more, such as two or more, three or more, four or more, five or more or ten or more nucleic acid constructs of the invention. The T-cell may comprise one or more, such as two or more, three or more, four or more, five or more or ten or more vectors of the invention. When the T-cell comprises two or more nucleic acid sequences, nucleic acid constructs or vectors, the two or more sequences, constructs or vectors may be the same or different.

Methods for producing the T-cell of the invention are set out below. The T-cell is typically produced from a human T-cell. The T-cell of the invention is therefore typically human. Alternatively, the T-cell may be produced from a T-cell from another animal or mammal, for instance from a commercially farmed animal, such as a horse, cattle, a sheep or a pig, from a laboratory animal, such as a mouse or a rat, or from a pet animal, such as a cat, a dog, a rabbit or a guinea pig. The T-cell may therefore be equine, bovine, ovine, porcine, murine, feline, leporine or cavine. The T-cell may be produced from a haematopoietic stem cell. Thus, the T-cell may be produced from cord blood. The T-cell may be produced from an embryonic stem cell, or an induced pluripotent stem cell (iPS cell).

The T-cell may have reduced or completely eliminated expression of native TCR. Accordingly, the T-cell may have a reduced or completely eliminated capacity to induce GVHD following administration to a HLA-mismatched recipient or patient.

Methods

The invention also provides a method for producing a T-cell expressing a molecule of the invention. The method comprises: transfecting or transducing a T-cell with a nucleic acid sequence of the invention or a nucleic acid construct of the invention; and expressing the molecule in the T-cell.

The T-cell that is transfected or transduced is typically a human T-cell. The human T-cell is typically from a donor that is HLA-matched or HLA-mismatched compared to a patient into which the resultant T-cell will be administered, or from a pool or bank of donor T-cells. The T-cell may alternatively be from another animal or mammal, for instance from a commercially farmed animal (such as a horse, cattle, a sheep or a pig), a laboratory animal (such as a mouse or a rat), or from a pet animal (such as a cat, a dog, a rabbit or a guinea pig). In this instance, when the resultant T-cell is administered to a patient, the patient is typically the same type of animal or mammal as that from which the initial T-cell is obtained.

The T-cell may be derived from a haematopoietic stem cell. Thus, the T-cell may be from cord blood. The T-cell may be derived from an embryonic stem cell, or an induced pluripotent stem cell (iPS cell).

The T-cell may be any type of T-cell that expresses a TCR comprising an alpha-chain and a beta-chain. T-cell types are described in detail above with reference to the T-cell of the invention. Preferably, the T-cell is a CAR T-cell.

The T-cell is typically obtained from the donor using leucapheresis. The T-cell may be sorted from the product of leucaphereis, for example if a mixed population of leukocytes or lypmhocytes is obtained from leucapheresis. T-cells may be isolated from the leucapheresis product using any means known in the art. For instance, T-cells may be sorted from the product using FACS or magnetic-activated cell sorting (MACS).

The T-cell provided may be obtained from a sample taken from the donor. The sample is typically a blood sample. The sample may be a bone marrow sample, or a sample of a lymphoid tissue such as a lymph node, tonsil, spleen or thymus. If the sample is obtained from bone marrow or a lymphoid tissue, the cells in the sample may need to be dissociated to allow T-cells to be isolated. Methods for dissociating bone marrow and lymphoid tissues are known in the art, but may include maceration (for example, maceration through a cell strainer) or enzymatic digestion. T-cells may be isolated from the sample or dissociated sample using any means known in the art. For instance, T-cells may be sorted from the sample using FACS or magnetic-activated cell sorting (MACS).

T-cells obtained from the donor may be expanded prior to use in the method of the invention. Expansion may involve stimulating the T-cells using an agonist for the TCR/CD3 complex, such as an anti-CD3 antibody, and/or an agonist for CD28 signalling, such as an anti-CD28 agonist. The anti-CD3 antibody and/or the anti-CD28 antibody may be loaded to a bead or other particle. Culture conditions for T-cell expansion are well known in the art.

Once provided, the T-cell is transfected or transduced with a nucleic acid sequence of the invention or a nucleic acid construct of the invention. Nucleic acid sequences and nucleic acid constructs are described in detail above.

The term "transduction" may be used to describe virus-mediated nucleic acid transfer. A viral vector may be used to transduce the cell with the one or more constructs. Conventional viral based expression systems could include retroviral, lentivirus, adenoviral, adeno-associated (AAV) and herpes simplex virus (HSV) vectors for gene transfer. Methods for producing and purifying such vectors are know in the art. The vector is preferably a vector of the invention. The T-cell may be transduced using any method known in the art. Transduction may be in vitro or ex vivo.

The term "transfection" may be used to describe non-virus-mediated nucleic acid transfer. The T-cell may be transfected using any method known in the art. Transfection may be in vitro or ex vivo. Any vector capable of transfecting the T-cell may be used, such as conventional plasmid DNA or RNA transfection. A human artificial chromosome and/or naked RNA and/or siRNA may be used to transfect the cell with the nucleic acid sequence or nucleic acid construct. Human artificial chromosomes are described in e.g. Kazuki et al., Mol. Ther. 19 (9): 1591-1601 (2011), and Kouprina et al., Expert Opinion on Drug Delivery 11 (4): 517-535 (2014). Alternative non-viral delivery systems include DNA plasmids, naked nucleic acid, and nucleic acid complexed with a delivery vehicle, such as a liposome. Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Nanoparticle delivery systems may be used to transfect the cell with the nucleic acid sequence or nucleic acid construct. Such delivery systems include, but are not limited to, lipid-based systems, liposomes, micelles, microvesicles and exosomes. With regard to nanoparticles that can deliver RNA, see, e.g., Alabi et al., Proc Natl Acad Sci USA. 2013 Aug. 6; 110 (32): 12881-6; Zhang et al., Adv Mater. 2013 Sep. 6; 25(33):4641-5; Jiang et al., Nano Lett. 2013 Mar. 13; 13 (3): 1059-64; Karagiannis et al., ACS Nano. 2012 Oct. 23; 6 (10):8484-7; Whitehead et al., ACS Nano. 2012 Aug. 28; 6 (8):6922-9 and Lee et al., Nat Nanotechnol. 2012 Jun. 3; 7 (6):389-93. Lipid Nanoparticles, Spherical Nucleic Acid (SNA(tm)) constructs, nanoplexes and other nanoparticles (particularly gold nanoparticles) are also contemplated as a means for delivery of a construct or vector in accordance with the invention.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectAmine, fugene and transfectam.

The T-cell may be transfected under suitable conditions. The T-cell and agent or vector may, for example, be contacted for between five minutes and ten days, preferably from an hour to five days, more preferably from five hours to two days and even more preferably from twelve hours to one day.

The nucleic acid sequence or nucleic acid construct transduced or transfected into the T-cell gives rise to expression of the molecule of the invention in the T-cell. As set out above, the nucleic acid construct may comprise a sequence encoding a CAR and/or a sequence encoding a suicide gene, in addition to the sequence encoding the molecule of the invention. Thus, the nucleic acid construct transduced or transfected into the T-cell may also give rise to expression of the CAR and/or the suicide gene. The nucleic acid sequence or nucleic acid construct preferably comprises a promoter which is operably linked to the one or more of the encoded sequences, and which is active in the T-cell or which can be induced in the T-cell.

The invention further provides a method for reducing or completely eliminating expression of native TCR in a T-cell, comprising (a) providing a nucleic acid sequence of the invention or a nucleic acid construct of the invention, or a vector encoding the nucleic acid sequence or nucleic acid construct; (b) transfecting or transducing the T-cell with the nucleic acid sequence, nucleic acid construct or vector; and (c) expressing the molecule in the T-cell. The method may be conducted in vivo. Preferably, the method is conducted in vitro. T-cells, nucleic acid sequences, nucleic acid constructs, vectors, transfection, transduction and expression are discussed in detail above. The T-cell is preferably a CAR T-cell. CAR T-cells are described in detail above. The CAR T-cell may be specific for one or more tumor antigens, for example one or more antigens associated with AML. The CAR T-cell may be specific for one or more of CD33, CD123 and CLL1. The resulting T-cell may have a reduced or completely eliminated capacity to cause GVHD following administration to a HLA-mismatched recipient or patient.

The invention also provides a method for producing a T-cell having reduced or completely eliminated expression of native TCR, comprising (a) providing a T-cell; (b) transfecting or transducing the T-cell with a nucleic acid sequence of the invention or a nucleic acid construct of the invention, or a vector encoding the nucleic acid sequence or nucleic acid construct; and (c) expressing the molecule in the T-cell. T-cells, nucleic acid sequences, nucleic acid constructs, vectors, transfection, transduction and expression are discussed in detail above. The T-cell produced by the method may be a CAR T-cell, as described in detail above. In this case, the T-cell provided may be transfected or transduced with a nucleic acid construct comprising a first nucleic acid sequence encoding the molecule of the invention, a second nucleic acid sequence encoding a CAR and, optionally, a third nucleic acid sequence encoding a suicide gene, or a vector comprising the construct. As mentioned above, the advantage of producing CAR T-cells having reduced or completely eliminated expression of native TCR in this way is that CAR expression is linked to expression of the molecule that inhibits native TCR expression and, optionally, expression of the suicide gene. Sorting on the expression of one marker therefore also sorts for expression of the other marker(s).

Medicaments, Methods and Therapeutic Use

The invention provides a method of reducing or preventing graft versus host disease (GVHD) in a patient associated with the administration of one or more allogeneic CAR T-cells to the patient, comprising (a) transfecting or transducing the one or more CAR T-cells with a nucleic acid sequence of the invention or a nucleic acid construct of the invention, or a vector encoding the nucleic acid sequence or nucleic acid construct; and (b) administering the CAR T-cells to the patient. The invention also provides a nucleic acid sequence of the invention or a nucleic acid construct comprising a first nucleic acid sequence of the invention and a second nucleic acid sequence which encodes a suicide gene for use in a method of reducing or preventing GVHD in a patient associated with the administration of one or more CAR T-cells to the patient, the method comprising (a) transfecting or transducing the one or more CAR T-cells with the nucleic acid sequence or nucleic acid construct and (b) administering the CAR T-cells to the patient. In these aspects, the invention relates to reducing the ability of therapeutic CAR T-cells to cause GVHD in a patient.

The invention also provides a method of reducing or preventing GVHD in a patient associated with the transfusion of one or more CAR T-cells to the patient, comprising (a) generating the one or more CAR T-cells by transfecting or transducing one or more T-cells with a nucleic acid construct comprising a first nucleic acid sequence of the invention and a second nucleic acid sequence which encodes a chimeric antigen receptor, or a vector encoding the nucleic acid construct; and (b) administering the CAR T-cells to the patient. In addition, the invention provides a nucleic acid construct comprising a first nucleic acid sequence of the invention and a second nucleic acid sequence which encodes a chimeric antigen receptor for use in a method of reducing or preventing GVHD in a patient associated with the administration of one or more CAR T-cells to the patient, the method comprising (a) generating the one or more CAR T-cells by transfecting or transducing one or more T-cells with the nucleic acid construct and (b) administering the CAR T-cells to the patient. In these aspects, the invention relates to the production of CAR T-cells having a reduced ability to cause GVHD in a patient.

The invention further provides a method of reducing or preventing GVHD in a patient associated with the transfusion of one or more CAR T-cells to the patient, comprising (a) producing one or more T-cells expressing a molecule of the invention by (i) providing one or more T-cells; (ii) transfecting or transducing the one or more T-cells with a nucleic acid sequence of the invention or a nucleic acid construct comprising a first nucleic acid sequence of the invention and a second nucleic acid sequence which encodes a suicide gene, or a vector encoding the nucleic acid sequence or nucleic acid construct; and (iii) expressing the molecule in the one or more T-cells; (b) converting the one or more T-cells into one or more CAR T-cells by transfecting or transducing the one or more T-cells with a construct encoding a CAR and expressing the CAR; and (c) administering the CAR T-cells to the patient. Thus, in this aspect, the invention relates to directing a T-cell having reduced ability to cause GVHD in a patient towards an antigen of interest in the patient.

GVHD may be reduced in one or more ways. Firstly, "reducing GVHD" may refer to reducing the incidence of GVHD in patients transfused or administered with one or more CAR T-cells. For example, the incidence of GVHD may be reduced in patients transfused or administered with one or more CAR T-cells transfected or transduced with a nucleic acid sequence or nucleic acid construct of the invention compared to patients transfused or administered with one or more CAR T-cells that is neither transfected nor transduced with a nucleic acid sequence or nucleic acid construct of the invention.

Secondly, "reducing GVHD" may refer to reducing the severity of GVHD in patients transfused or administered with one or more CAR T-cells. For instance, the severity of GVHD may be reduced in patients transfused or administered with one or more CAR T-cells transfected or transduced with a nucleic acid sequence or nucleic acid construct of the invention compared to patients transfused or administered with one or more CAR T-cells that is neither transfected nor transduced with a nucleic acid sequence or nucleic acid construct of the invention. In particular, the patients may experience fewer clinical signs of GVHD, or less severe clinical signs of GVHD. The patients may experience a lower grade and/or stage of GVHD.

In these ways, the potential of therapeutic CAR T-cells to cause undesirable side effects in an HLA (or equivalent) -mismatched patient can be minimised. The resultant CAR T-cell product may therefore be used off-the-shelf in any patient in need thereof, regardless of the patient's HLA (or equivalent) type. Accordingly, the methods of the invention permit the production of an improved and safer CAR T-cell product.

The patient may be any suitable patient. The patient is generally a human patient. The patient may be any of the animals or mammals mentioned above with reference to the source of the T-cells.

The CAR may be any suitable CAR. Suitable CARs are described above with reference to the construct of the invention. In particular, the CAR may comprise an antigen recognition domain that is specific for a tumour antigen, a viral antigen, a bacterial antigen, a fungal antigen, a protozoal antigen, a host antigen or a cytokine. The antigen recognition domain is preferably specific for a tumour antigen, such as an antigen associated with AML. The antigen recognition domain may be specific for an antigen associated with any of the diseases discussed below.

Nucleic acid sequences and constructs, vectors, and transfection, transduction and expression are discussed in detail above.

The invention provides a method of treating a disease in a patient in need thereof, comprising administering to the patient a therapeutically effective number of CAR T-cells expressing a molecule of the invention. Similarly, the invention provides CAR T-cells expressing a molecule of the invention, for use in a method of treating a disease in a patient in need thereof, the method comprising administering to the patient a therapeutically effective number of cells.

The disease may be any disease in which the patients may benefit from antigen-specific T-cell responses. For instance, the disease may be a disease in which the subject may benefit from increased cytotoxic, helper or gamma delta T-cell responses. The disease may be an infection, such as a bacterial, viral, fungal, protozoal or other parasitic infection. Preferably, the disease is cancer. The cancer may be anal cancer, bile duct cancer (cholangiocarcinoma), bladder cancer, blood cancer, bone cancer, bowel cancer, brain tumours, breast cancer, colorectal cancer, cervical cancer, endocrine tumours, eye cancer (such as ocular melanoma), fallopian tube cancer, gall bladder cancer, head and/or neck cancer, Kaposi's sarcoma, kidney cancer, larynx cancer, leukaemia, liver cancer, lung cancer, lymph node cancer, lymphoma, melanoma, mesothelioma, myeloma, neuroendocrine tumours, ovarian cancer, oesophageal cancer, pancreatic cancer, penis cancer, primary peritoneal cancer, prostate cancer, Pseudomyxoma peritonei, skin cancer, small bowel cancer, soft tissue sarcoma, spinal cord tumours, stomach cancer, testicular cancer, thymus cancer, thyroid cancer, trachea cancer, unknown primary cancer, vagina cancer, vulva cancer or endometrial cancer. The leukaemia is preferably acute lymphoblastic leukaemia, acute myeloid leukaemia (AML), chronic lymphocytic leukaemia or chronic myeloid leukaemia. The lymphoma may be Hodgkin lymphoma or non-Hodgkin lymphoma. The cancer may be primary cancer or secondary cancer. Preferably, the cancer is leukaemia. Most preferably, the cancer is AML. When the cancer is AML, the one or more CAR T-cells are preferably specific for one or more of CD33, CD 123 and CLL1.

When the cancer is AML, it may be advantageous for the expression of native TCR in the CAR T-cells to be reduced rather than completely eliminated. By allowing some native TCR expression to remain, administration of the CAR T-cells to the patient may be associated with a small amount of GVHD. This weak GVHD may be of benefit to the patient, as it may non-specifically attack the bone marrow compartment, killing AML cells and their precursors. Non-specific attack of the marrow compartment may necessitate the provision of a rescue allograft to the patient. However, as administration of CAR T-cells targeting one or more of CD33, CD 123 and CLL1 may cause myeoloablation and necessitate rescue allograft in any case, the residual retention of native TCR expression in such CAR T-cells does not have any particular disadvantages.

The disease may be a disease in which the subject may benefit from increased regulatory T-cell responses to an antigen. The disease may be an allergic disease, such as atopic dermatitis, allergic airway inflammation or perennial allergic rhinitis. The disease is preferably an autoimmune condition, such as alopecia areata, autoimmune encephalomyelitis, autoimmune hemolytic anemia, autoimmune hepatitis, dermatomyositis, diabetes (type 1), autoimmune juvenile idiopathic arthritis, glomerulonephritis, Graves' disease, Guillain-Barre syndrome, idiopathic thrombocytopenic purpura, myasthenia gravis, autoimmune myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, autoimmune thyroiditis, uveitis or vitiligo. The disease is preferably GVHD.

The T-cells or CAR T-cells of the invention may be provided as a pharmaceutical composition. The pharmaceutical composition preferably comprises a pharmaceutically acceptable carrier or diluent. The pharmaceutical composition may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, 19th Edition, Mack Publishing Company, Eastern Pa., USA.

The T-cells, CAR T-cells or pharmaceutical composition may be administered by any route. Suitable routes include, but are not limited to, intravenous, intramuscular, intraperitoneal or other appropriate administration routes. The T-cells, CAR T-cells or pharmaceutical composition is preferably administered intravenously.

Compositions may be prepared together with a physiologically acceptable carrier or diluent. Typically, such compositions are prepared as liquid suspensions of cells. The cells may be mixed with 25 an excipient which is pharmaceutically acceptable and compatible with the active ingredient. Suitable excipients are, for example, water, saline, dextrose, glycerol, of the like and combinations thereof.

In addition, if desired, the pharmaceutical compositions of the invention may contain minor amounts of auxiliary substances such as wetting or emulsifying agents, pH buffering agents, and/or adjuvants which enhance effectiveness. The composition preferably comprises human serum albumin. 30

One suitable carrier or diluents is Plasma-Lyte A®. This is a sterile, nonpyrogenic isotonic solution for intravenous administration. Each 100 mL contains 526 mg of Sodium Chloride, USP (NaCl); 502 mg of Sodium Gluconate (C6H11NaO7); 368 mg of Sodium Acetate Trihydrate, USP (C2H3NaO2·3H2O); 37 mg of Potassium Chloride, USP (KCl); and 30 mg of Magnesium Chloride, USP (MgCl2·6H2O). It contains no antimicrobial agents. The pH is adjusted with sodium hydroxide. The pH is 7.4 (6.5 to 8.0).

The T-cells or CAR T-cells are administered in a manner compatible with the dosage formulation and in such amount will be therapeutically effective. The quantity to be administered depends on the subject to be treated, the disease to be treated, and the capacity of the subject's immune system. Precise amounts of T-cells or CAR T-cells required to be administered may depend on the judgement of the practitioner and may be peculiar to each subject.

Any suitable number of T-cells or CAR T-cells may be administered to a subject. For example, at least, or about, $0.2 \times 10^6$, $0.25 \times 10^6$, $0.5 \times 10^6$, $1.5 \times 10^6$, $4.0 \times 10^6$ or $5.0 \times 106$ cells per kg of patient may administered. For example, at least, or about, $10^5$, $10^6$, $10^7$, $10^8$, $10^9$ cells may be administered. As a guide, the number of cells of the invention to be administered may be from $10^5$ to $10^9$, preferably from $10^6$ to $10^8$. Typically, up to $2 \times 10^8$ IMP cells are administered to each patient. In such cases where cells are administered or present, culture medium may be present to facilitate the survival of the cells. In some cases the cells of the invention may be provided in frozen aliquots and substances such as DMSO may be present to facilitate survival during freezing. Such frozen cells will typically be thawed and then placed in a buffer or medium either for maintenance or for administration.

The following Examples illustrate the invention.

EXAMPLES

Example 1

Knockdown of the TCR/CD3 Complex

ScFvs were cloned into a retroviral transfer vector in frame at their amino-terminus with a signal peptide and with the SEKDEL (SEQ ID NO:20) motif at their carboxy terminus. An internal ribosomal entry sequence (IRES) was cloned after the scFv-SEKDEL. A fluorescent protein was cloned after the IRES. 293T cells were transfected with the transfer vectors along with an expression plasmid coding for the RD114 envelope and a further expression plasmid which supplies gamma-retroviral gagpol. After 48 and 72 hours, supernatant was harvested. T-cell lines were transduced by exposing the T-cells to the supernatant in the presence of retronectin. Primary human T-cells were transduced in a similar manner but were stimulated with anti-CD3 and anti-CD28 and IL2 beforehand. To determine TCR surface expression, T-cells were stained with fluorescent monoclonal antibodies which recognize CD3/TCR, washed and analysed by flow-cytometry.

In initial experiments, the scFvs from hybridomas OKT3 and BMA031 were used. Some reduction in TCR expression was noted (FIG. 1). In addition, TCR knockdown in non-transduced T-cells in the same culture system were observed. This suggested that the scFv was leaking out of the cells and blocking staining for the TCR rather than blocking its maturation and exit to the cell surface.

Figure 3B:
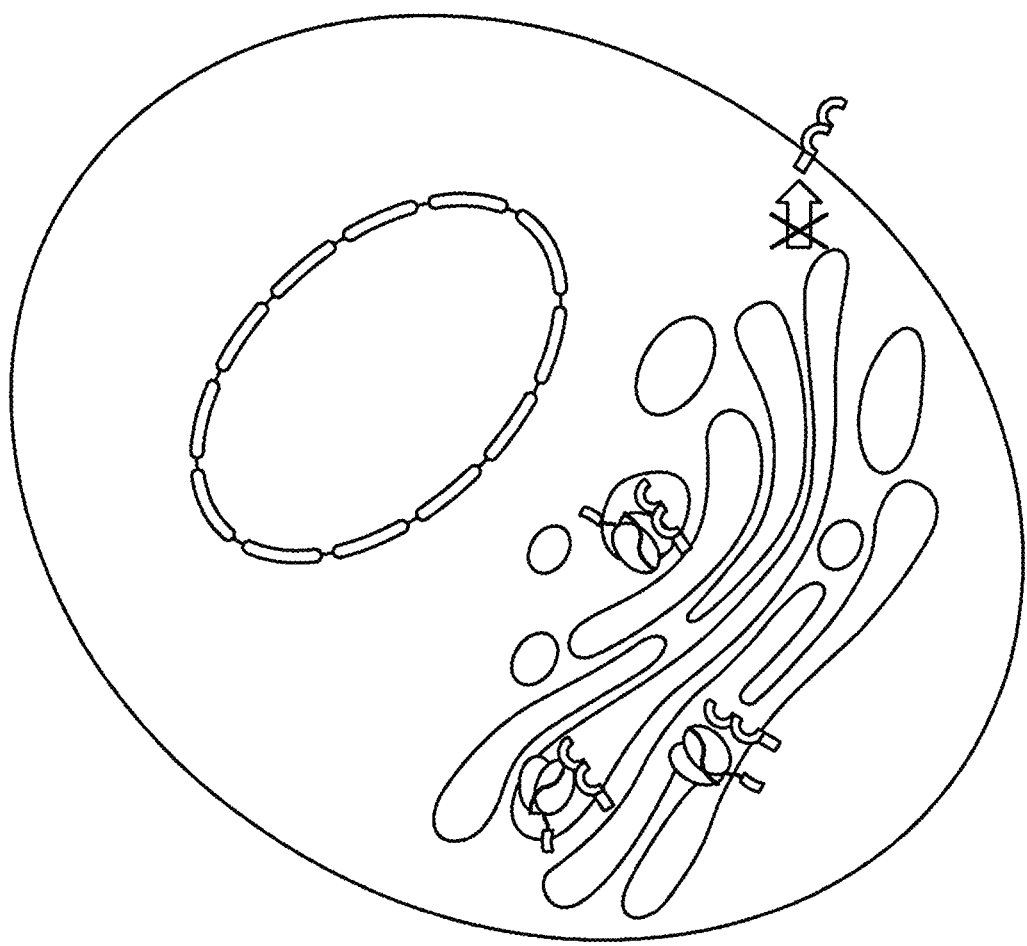

Consequently, similar constructs were generated from other anti-TCR/CD3 hybridomas. These were carefully selected from the literature on the basis that they are known to be able to stain intracellularly—hence being able to recognize the assembling TCR/CD3 complex in a nascent stage before access to the Golgi has passed. The anti-TCR/CD3 antibody UCHT1 (Beverley, P. C. & Callard, R. E. Distinctive functional characteristics of human 'T' lymphocytes defined by E resetting or a monoclonal anti-T cell antibody. Eur. J. Immunol. 11, 329-334 (1981)) was chosen for this application. FIG. 2 shows the amino acid sequence of the S-UCHT1-KDEL molecule. FIG. 3a depicts the structure of this molecule, and FIG. 3b shows its presumed mechanism of action.

Figure 4B:
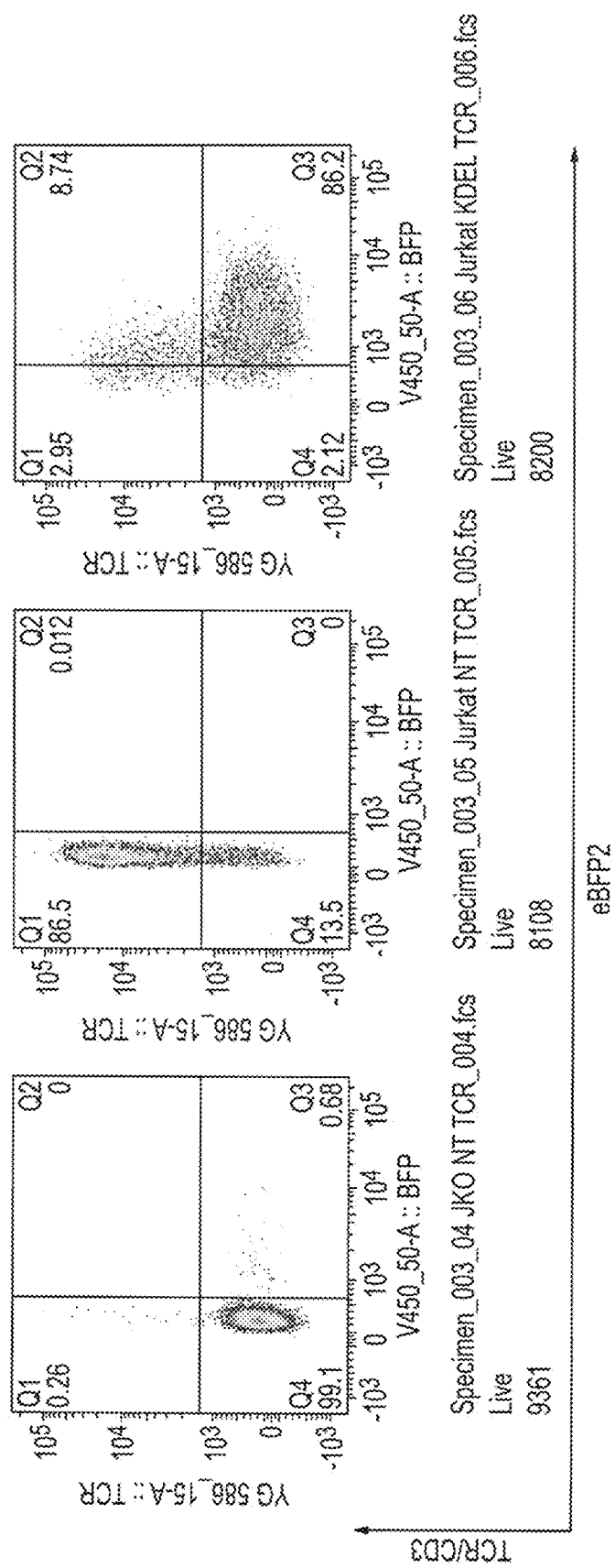
(FIG. 4a) TCR negative Jurkats and (FIG. 4b) wt Jurkats transduced with S-UCHT1-sekdel. Marker gene (eBFP2) is shown on the x-axis. Transduced cells (i.e. eBFP2 cells) are TCR negative.

Jurkat T-cells were transduced with this construct and stained with anti-TCR/CD3 antibodies. The retention protein was co-expressed with the fluorescent marker protein eBFP2. The clone of staining antibody was carefully chosen as to not compete with UCHT1 binding. As a control, Jurkat T-cells which have had their TCR alpha and beta chain genes disrupted were also stained. Complete reduction of surface TCR was observed in transduced (but not non-transduced Jurkat T-cells) (FIGS. 4a and 4b).

Figure 5:
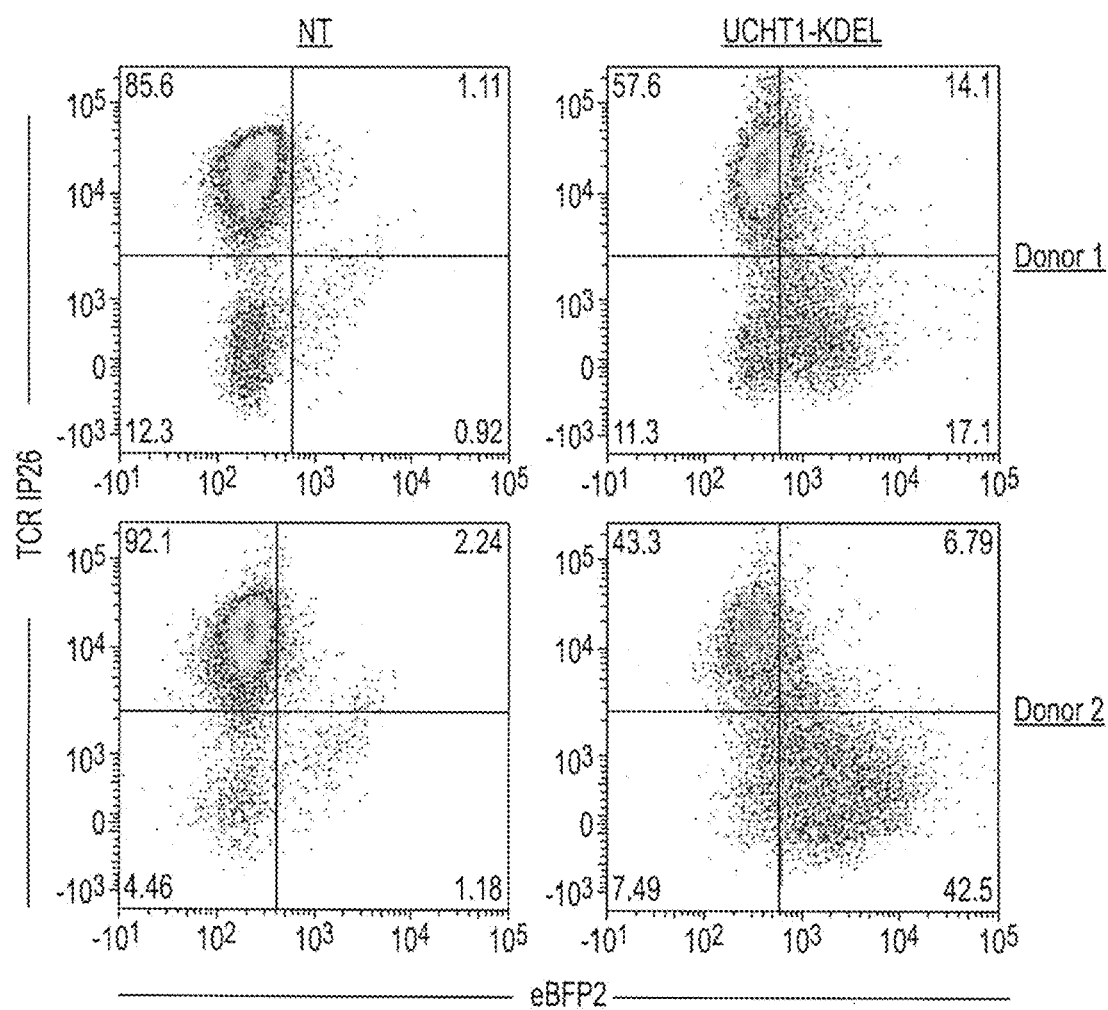
FIG. 5. Peripheral blood from two normal donors are transduced with S-UCHT1-sekdel.

Peripheral blood T-cells from normal donors were transduced with UCHT1-sekdel. Transduced T-cells were stained with a non-cross-reactive anti-CD3/TCR mAb and analysed by flow-cytometry. Lack of TCR expression was seen on T-cells expressing the marker gene (FIG. 5). Fluorescent signal was down to that of isotype control in this population.

The invention claimed is:

1. A molecule which disrupts the expression of native T cell receptor (TCR) on the surface of a T cell, which molecule comprises a binding portion comprising a binding domain which binds to one or more components of the TCR/CD3 complex and which is a UCHT1 antibody or a Jovi.1 antibody or is derived from a UCHT1 antibody or a Jovi.1 antibody, and a retention portion comprising a retention domain that intracellularly retains the one or more components within the endoplasmic reticulum (ER) or Golgi apparatus and which is a KDEL sequence, wherein the retention domain is in frame at the C-terminal to the binding domain, and wherein the binding domain comprises:

(a) three heavy chain complementarity determining regions (CDRs) (HCDR1, HCDR2 and HCDR3) contained within the heavy chain variable region (HCVR) sequence of SEQ ID NO: 7, and three light chain CDRs (LCDR1, LCDR2 and LCDR3) contained within the light chain variable region (LCVR) sequence of SEQ ID NO: 8; or (b) three heavy chain CDRs (HCDR1, HCDR2 and HCDR3) contained within the HCVR sequence of SEQ ID NO: 15, and three light chain CDRs (LCDR1, LCDR2 and LCDR3) contained within the LCVR sequence of SEQ ID NO: 16.

2. A molecule according to claim 1, wherein the one or more components are not assembled to form the TCR/CD3 complex.

3. A molecule according to claim 1, wherein the binding domain is a single chain variable fragment (scFv) , a scFv-Fc, a single-domain antibody, or a monoclonal antibody.

4. A molecule according to claim 3, wherein the single-domain antibody is a camelid antibody, an artificial $V_H$H fragment or an immunoglobulin new antigen receptor (IgNAR).

* * * * *